(12) United States Patent
Fonger et al.

(10) Patent No.: US 11,229,454 B2
(45) Date of Patent: Jan. 25, 2022

(54) ACCESS DEVICES AND METHODS FOR TREATMENT OF MEDICAL CONDITIONS AND DELIVERY OF INJECTABLES

(71) Applicant: CARDIOSCOUT SOLUTIONS, INC., Marietta, GA (US)

(72) Inventors: James D. Fonger, Atlanta, GA (US); Gary H. Sanders, Rancho Santa Margarita, CA (US); Jack Greelis, Carlsbad, CA (US); Matthew Thomas Yurek, San Diego, CA (US)

(73) Assignee: CARDIOSCOUT SOLUTIONS, INC., Marietta, GA (US)

( * ) Notice: Subject to any disclaimer, the term of this patent is extended or adjusted under 35 U.S.C. 154(b) by 725 days.

(21) Appl. No.: 15/587,219

(22) Filed: May 4, 2017

(65) Prior Publication Data

US 2017/0319233 A1 Nov. 9, 2017

Related U.S. Application Data

(60) Provisional application No. 62/332,941, filed on May 6, 2016.

(51) Int. Cl.
*A61B 1/05* (2006.01)
*A61B 17/34* (2006.01)
(Continued)

(52) U.S. Cl.
CPC ........ *A61B 17/3421* (2013.01); *A61B 1/0052* (2013.01); *A61B 1/00082* (2013.01); *A61B 1/00087* (2013.01); *A61B 1/00089* (2013.01); *A61B 1/00094* (2013.01); *A61B 1/00098* (2013.01); *A61B 1/01* (2013.01); *A61B 1/018* (2013.01); *A61B 1/05* (2013.01); *A61B 1/0684* (2013.01); *A61B 1/07* (2013.01); *A61B 1/12* (2013.01); *A61B 1/3137* (2013.01); *A61B 8/12* (2013.01); *A61B 17/00234* (2013.01);
(Continued)

(58) Field of Classification Search
CPC ... A61B 17/3415; A61B 1/00094; A61B 8/12; A61B 90/361; A61B 1/00137; A61B 1/0014; A61B 1/00098; A61B 2017/3454; A61B 17/3421; A61B 1/05
See application file for complete search history.

(56) References Cited

U.S. PATENT DOCUMENTS 8,771,173 B2   7/2014   Fonger et al.
9,173,705 B2   11/2015  Whayne et al.
(Continued)

OTHER PUBLICATIONS

International Search Report and Written Opinion from International Application No. PCT/US2017/031130 dated Sep. 15, 2017.

*Primary Examiner* — Joanne M Hoffman
*Assistant Examiner* — Milton Truong
(74) *Attorney, Agent, or Firm* — Meunier Carlin & Curfman LLC

(57) ABSTRACT

Disclosed are access devices that can be used to safely guide instruments, such as EP ablation catheters, to a therapy site such one within the pericardial space of the heart. The access devices include integrated visualization, illumination, stabilization, and safety features in a single platform that can, for example, more safely and efficiently identify and ablate several ventricular tachycardia (VT) locations on the left ventricle of the heart.

27 Claims, 18 Drawing Sheets

(51) Int. Cl.

| | | |
|---|---|---|
| *A61B 1/00* | (2006.01) | |
| *A61B 1/01* | (2006.01) | |
| *A61B 1/313* | (2006.01) | |
| *A61B 17/02* | (2006.01) | |
| *A61B 1/005* | (2006.01) | |
| *A61B 1/018* | (2006.01) | |
| *A61B 1/06* | (2006.01) | |
| *A61B 1/07* | (2006.01) | |
| *A61B 1/12* | (2006.01) | |
| *A61B 8/12* | (2006.01) | |
| *A61B 17/00* | (2006.01) | |
| *A61M 5/14* | (2006.01) | |
| *A61M 25/06* | (2006.01) | |
| *A61B 17/32* | (2006.01) | |
| *A61B 90/00* | (2016.01) | |
| *A61B 17/22* | (2006.01) | |
| *A61B 8/08* | (2006.01) | |
| *A61B 18/14* | (2006.01) | |
| *A61B 18/00* | (2006.01) | |

(52) U.S. Cl.
CPC ...... *A61B 17/0218* (2013.01); *A61B 17/3415* (2013.01); *A61B 17/3478* (2013.01); *A61M 5/14* (2013.01); *A61M 25/0662* (2013.01); *A61B 8/0858* (2013.01); *A61B 18/1492* (2013.01); *A61B 90/361* (2016.02); *A61B 2017/003* (2013.01); *A61B 2017/00243* (2013.01); *A61B 2017/00247* (2013.01); *A61B 2017/00292* (2013.01); *A61B 2017/00557* (2013.01); *A61B 2017/22039* (2013.01); *A61B 2017/22061* (2013.01); *A61B 2017/22071* (2013.01); *A61B 2017/320044* (2013.01); *A61B 2017/320048* (2013.01); *A61B 2017/3445* (2013.01); *A61B 2017/3454* (2013.01); *A61B 2018/00351* (2013.01); *A61B 2018/00577* (2013.01)

(56) References Cited

U.S. PATENT DOCUMENTS

| | | | |
|---|---|---|---|
| 2003/0168059 A1* | 9/2003 | Pacey | A61B 1/267 |
| | | | 128/200.26 |
| 2012/0046677 A1* | 2/2012 | Lin | A61B 17/00008 |
| | | | 606/159 |
| 2012/0165916 A1 | 6/2012 | Jordan | |
| 2012/0265094 A1 | 10/2012 | Goldfarb et al. | |
| 2012/0289858 A1* | 11/2012 | Ouyang | A61B 1/00124 |
| | | | 600/562 |
| 2014/0135576 A1 | 5/2014 | Herbert | |
| 2014/0275773 A1* | 9/2014 | Tarazona | A61M 25/0084 |
| | | | 600/106 |
| 2015/0045825 A1* | 2/2015 | Caplan | A61M 29/00 |
| | | | 606/191 |
| 2015/0173711 A1* | 6/2015 | Hiraoka | A61B 8/4494 |
| | | | 600/466 |
| 2015/0327754 A1 | 11/2015 | Leeflang et al. | |
| 2016/0038133 A1* | 2/2016 | Smith | A61B 1/00089 |
| | | | 600/204 |
| 2016/0235400 A1* | 8/2016 | Hiernaux | G02B 23/2476 |
| 2016/0249978 A1 | 9/2016 | Lee et al. | |

\* cited by examiner

ACCESS DEVICES AND METHODS FOR TREATMENT OF MEDICAL CONDITIONS AND DELIVERY OF INJECTABLES

RELATED APPLICATIONS

This patent application claims the benefit of U.S. Provisional Application No. 62/332,941 filed on May 6, 2016, entitled "Access Device for Cardiac Ablation," which is incorporated herein by this reference in its entirety.

FIELD OF THE INVENTION

This disclosure relates generally to medical devices and, in particular, devices for providing surgical access within the body of a patient.

BACKGROUND

Existing medical devices and techniques for accessing the internal organs and anatomy of patients to treat medical conditions and deliver injectables are inadequate for many circumstances. For example, cardiologists would like to be able to perform arrhythmia treatments (e.g., mappings, diagnostics, and ablations) and to be able to deliver injectables to treat various atrial fibrillation and other heart conditions. However, many instances of such medical conditions are complex in nature and cannot be handled with existing endocardial catheters providing treatment on the inside of the heart. Specifically, for example, there are a host of sources of ventricular tachycardia that are on the outside of the heart, for example, on the left ventricle and right ventricle on the lateral wall. In addition, there is muscle on the outside of the heart that could be treated with various pharmaceuticals or other injectables. Being able to access the outside of the heart instead of, or in addition to, the inside of the heart, could enable better treatment outcomes, reduce patient risk, and provide other benefits in many circumstances.

However, attempts to use existing endocardial devices to map, diagnose, and deliver therapies to the outside surface of the heart have revealed that those devices are not well suited for accessing the heart through the pericardium. The pericardium is a sac-like layer that surrounds and provides a protective, lubricated covering over the epicardium outside surface of the heart. The heart beats and otherwise moves within the pericardium, with the epicardium generally resting against the pericardium. Because of this contact, any device used within the pericardium must separate and navigate in the space between the pericardium and epicardium. Existing endocardial devices are not designed to create space, navigate, and remain stable in this context. During a procedure for example, the surface of the beating heart is in constant motion, beating 60, 70, or more beats per minute. Existing devices are unable to navigate to and deliver treatments and injectables to precise locations within the pericardium and adjacent to a beating heart.

Existing endocardial devices are also poorly suited for therapies on the outside of the heart because they rely on indirect imaging. For example, an endocardial procedure may involve a three-dimensional (3D) mapping system and/or fluoroscopy to provide images of the heart. However, such indirect imaging systems are ill-suited for navigating and treating the outside of the heart. Such systems do not enable adequate identification of many anatomical structures, such as fat pads, lesions, arteries, and vascular pads on the outside of the heart that often must be avoided. Similarly, it can be difficult to identify an ischemic patch for treatment using indirect visualization.

Existing endocardial devices are particularly ill suited for ablation procedures on the outside surface of the heart. For example, existing 7 French electrophysiology (EP) ablation catheters and indirect imaging modalities have been used in such procedures. The procedures involved using endocardial EP ablation catheters within the pericardium on the epicardial surface of the beating heart and directing them around the surface of the heart by following their progress on 2D fluoroscopy images and/or mapping the area using conventional 3D mapping systems. Using these devices there is no pericardial space creation, no illumination of that space, and no direct visualization of the surface of the beating heart. The ablating end of the EP catheter is also not stabilized relative to the surface of the heart. There is also no way to directly visualize the precise location that is being considered for ablation to confirm that there are no epicardial coronary arteries or other anatomical structures that should not be ablated at the intended ablation site.

There is a substantial need for one or more medical devices and methods for accessing the internal organs and anatomy of patients to treat medical conditions and deliver injectables in many circumstances. Such devices and methods are needed particularly in circumstances such as those that benefit from direct visualization, space creation, and/or stabilization within a space between two adjacent surfaces.

SUMMARY

Disclosed are access devices that can be used to safely guide instruments, such as EP ablation catheters, to a therapy site, such one within the pericardial space of the heart. The access devices include integrated visualization, illumination, stabilization, and safety features in a single platform that can, for example, more safely and efficiently identify and ablate several ventricular tachycardia (VT) locations on the left ventricle of the heart. In addition, the access devices can include integrated ultrasound (e.g., an ultrasound transducer), for example, to determine epicardial wall thickness and/or to facilitate tissue determinations between vascularized tissue and ischemic tissue.

The access devices disclosed herein facilitate improved medical techniques. For example, an exemplary access device can be introduced to the pericardium using a "dry" pericardial tap, micro-puncture technique, or modified Seldinger technique to establish guide wire access to the pericardial space. The access device can follow this guide wire into the pericardium. A camera in the access device can also provide visualization from insertion all the way to the heart or other organs for greater safety of administration. The device can be tapered to dilate the pericardium and allow the disclosed access device to enter the pericardial space. The device can elevate the neighboring pericardium with balloon inflation and/or using a hinged shell. Expanding a balloon or moving the hinged shell can help avoid damage to a phrenic nerve, improve visualization of the myocardium, and/or help stabilize the access device. An instrument, such as an EP ablation catheter, can then be introduced down the instrument channel of the access device to protrude out the distal end of the device. The camera in the access device can visualize the tip of the EP ablation catheter and confirm safe placement of the ablation tip before energizing the tip for ablation. The access device supporting the ablation catheter can additionally, or alternatively, connect to the beating surface of the heart using suction to further stabilize the ablation platform before treatment. The site can also be checked after treatment to confirm that no unexpected injury to the surface of the heart has occurred.

The details of one or more embodiments of the invention are set forth in the accompanying drawings and the description below. Other features, objects, and advantages of the invention will be apparent from the description and drawings, and from the claims.

DETAILED DESCRIPTION

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

Embodiments of the invention provide access devices that can be used to safely guide instruments, such as EP ablation catheters, to a therapy site, such as one within the pericardial space of the heart. The access devices can be used with already-approved catheters and newly-developed catheters to enhance the capabilities of those catheters. In one example, an access device provides an exoskeleton through which an already-approved catheter can be inserted to effectively provide vision, lighting, stability, navigation, and/or articulation capabilities to the catheter. In addition, attributes of an access device can effectively lift the pericardium off the heart to create working space, illuminate the working space, and provide direct visualization of that working space. In one example, a physician is able to view the working end of an ablation catheter relative to a treatment location in the working space under direct video vision. The video vision can also show the relation of the catheter to nearby epicardial structures. Such visibility provides numerous benefits. For example, showing the epicardial coronary (or at least portions of them) and/or the left atrial appendage allows the user to determine the precise location of the treatment and avoid treating unintended areas. In many instances, the view provides sufficient confidence to allow treatment to commence without needing to pause the procedures for confirmation via fluoroscopy, which can significantly reduce the time and risks associated with the procedures.

Figure 1:
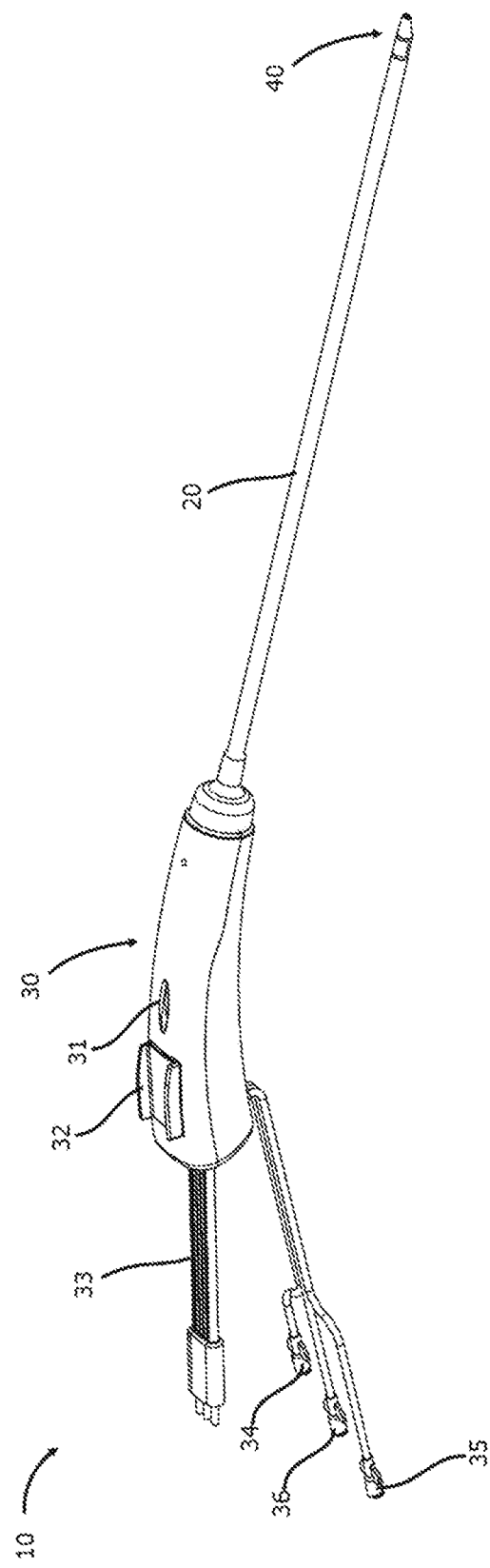
FIG. 1 is a perspective view of an access device of one embodiment of the disclosed surgical access device.
Figure 2:
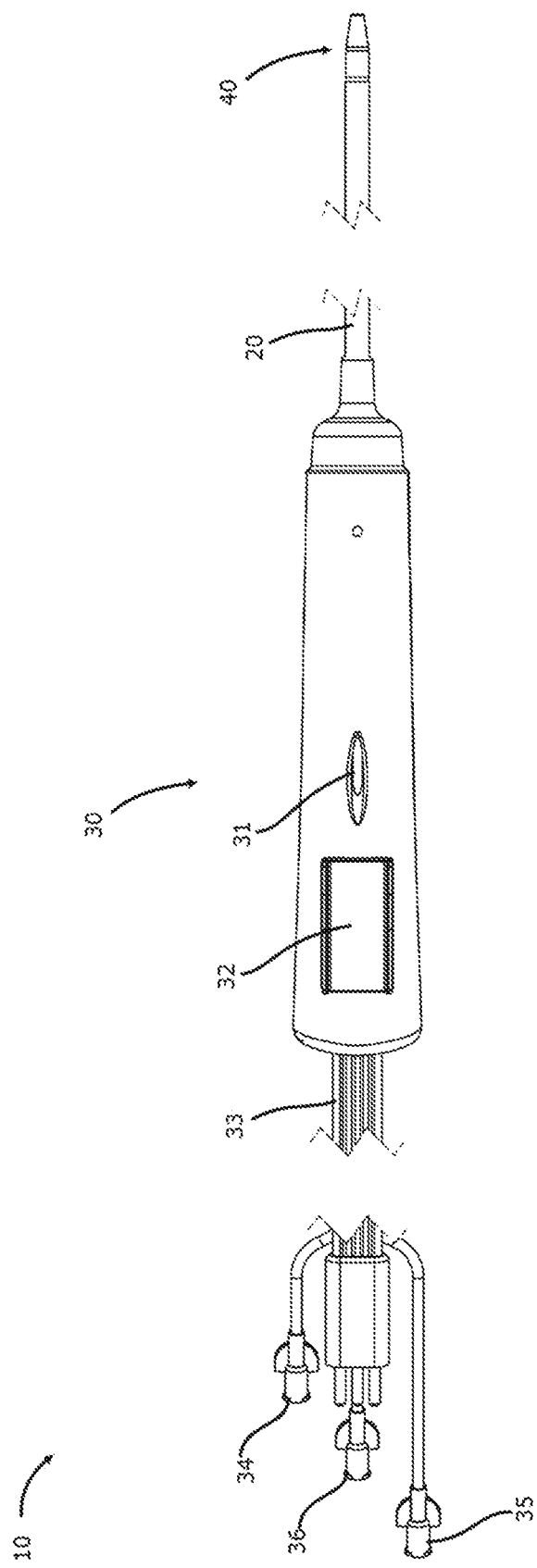
FIG. 2 is a top view of the access device of FIG. 1.
Figure 3:
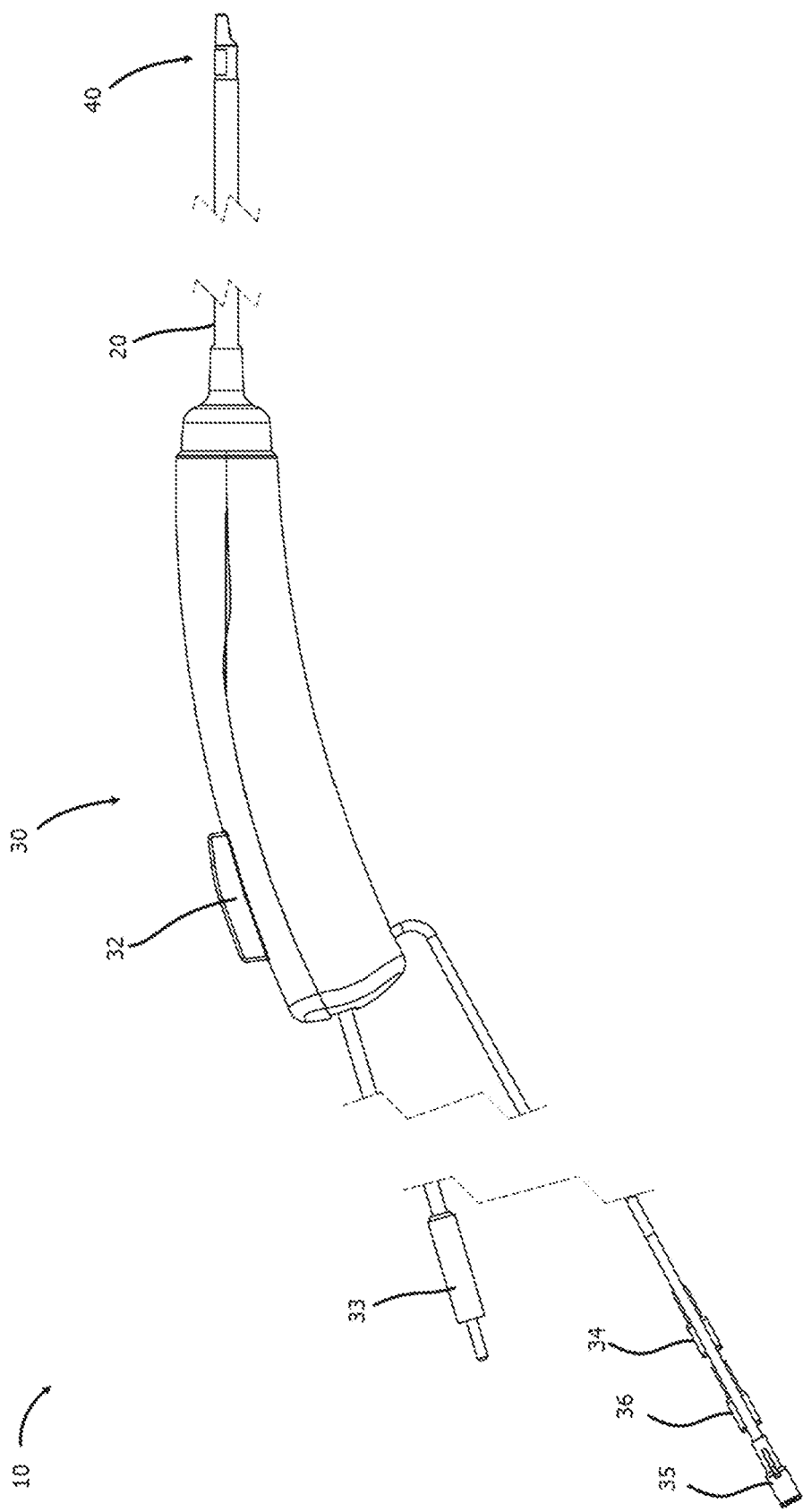
FIG. 3 is a side view of the access device of FIG. 1.

Referring to FIGS. 1-3, disclosed is an access device 10 for facilitating access, safety, stabilization, and visualization for cardiac ablation of the heart under the pericardium. The access device 10 generally includes a head portion 40, a shaft 20, and a handle portion 30.

It should be noted that although described in one embodiment as providing access to the heart for ablation, the access device may provide access to a range of tissue structures through varying pathways and for use with varying surgical instruments. For example, access could be provided to other organs, such as the liver, muscles, skeletal structures, etc. Some embodiments of the access device 10, however, are best-suited for providing various combinations of visualization and access through small openings (e.g., 2 cm or less through the skin and pericardium) during surgical procedures, cardiology procedures, or EP cardiology catheterization laboratory procedures on the heart.

As shown in FIGS. 1-3, the shaft 20 is attached to the handle portion 30 at its proximal end and to the head portion 40 at its distal end. The proximal end of the shaft 20 is configured to be manipulated from a position external to the patient's body (i.e., more "proximal" to the user). The distal end of the shaft 20 is sized and configured to insert through a relatively small opening in the patient's body, such as a 2 cm or smaller sub-xiphoid incision, or via percutaneous needle and guide wire access.

Figure 12:
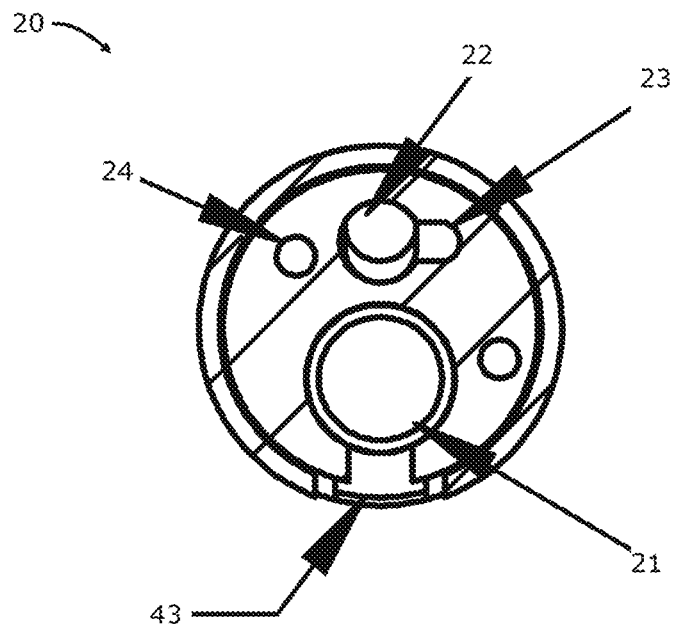
FIG. 12 is a vertical sectional view of a distal tip portion of the surgical access device of FIG. 6.
Figure 13:
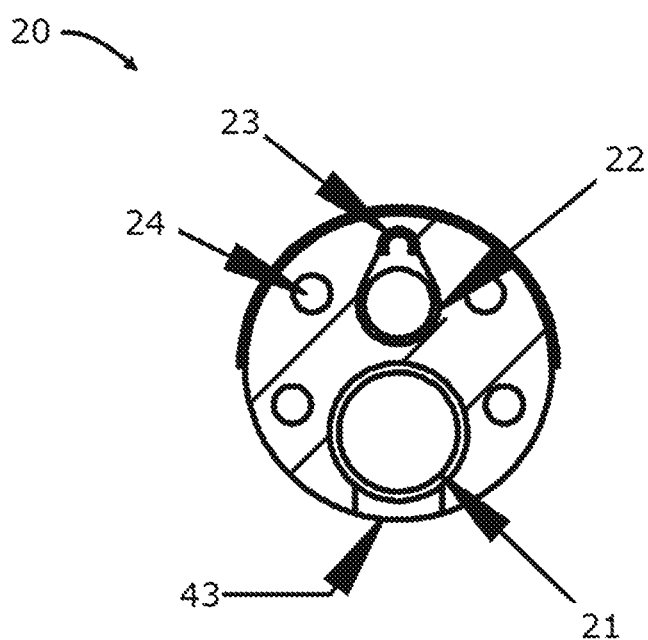
FIG. 13 is a vertical sectional view of a distal tip portion of the surgical access device of FIG. 7.
Figure 14:
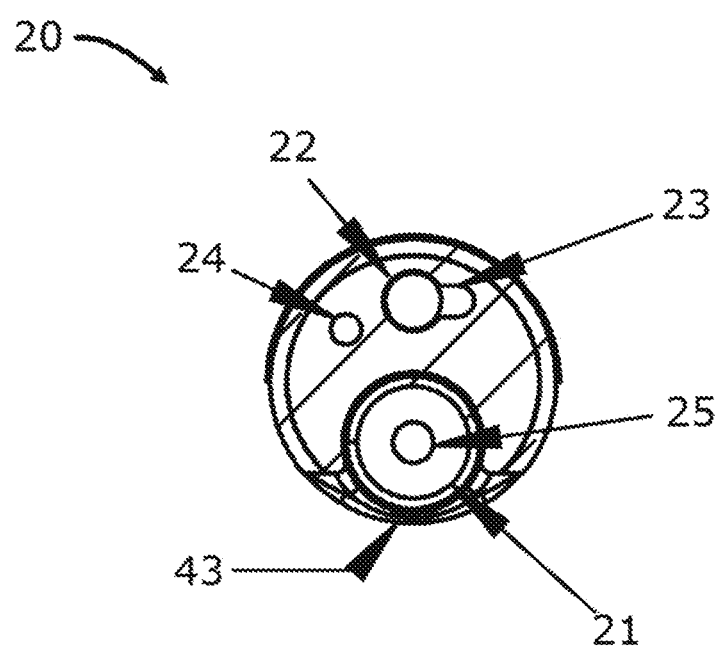
FIG. 14 is a vertical sectional view of a distal tip portion of the surgical access device of FIG. 8.

As further shown in FIGS. 12-14, the shaft 20 defines a lumen that contains one or more channels extending longitudinally there through. Examples of channels that can extend through the lumen of the shaft 20 include, but are not limited to, an instrument channel 21, a camera channel 22, a camera flush line 23, a balloon inflation channel 24, and a guide wire channel 25. In some cases, the lumen of the shaft 20 contains a distinct vacuum line channel, but in other cases, the lumen of the catheter shaft serves as the vacuum line channel. Preferably, the outer diameter of the shaft 20 is from 10 mm to 20 mm, including about 5, 10, 15, or 20 mm. The instrument channel 21 can extend proximally from the head portion 40, through the shaft 20, into the handle portion 30, optionally terminating at an instrument portal 31 within the handle portion 30.

Figure 15:
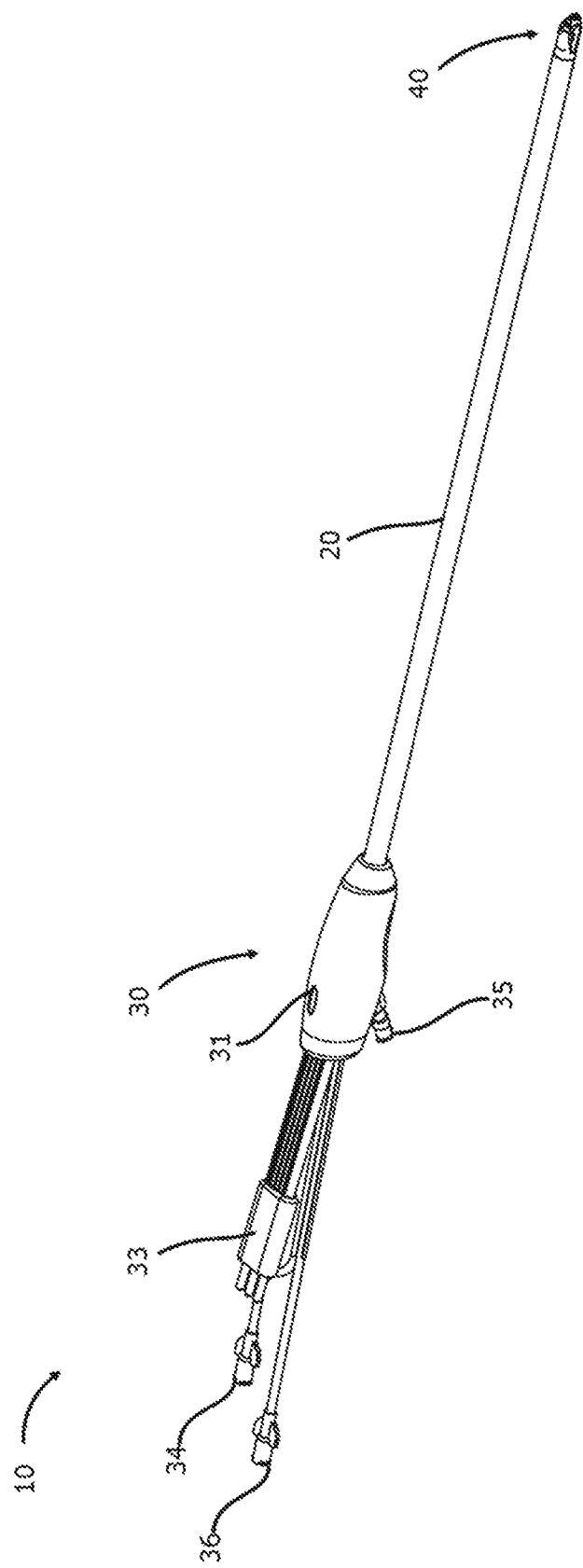
FIG. 15 is a perspective view of an access device of one embodiment of the disclosed surgical access device.
Figure 16:
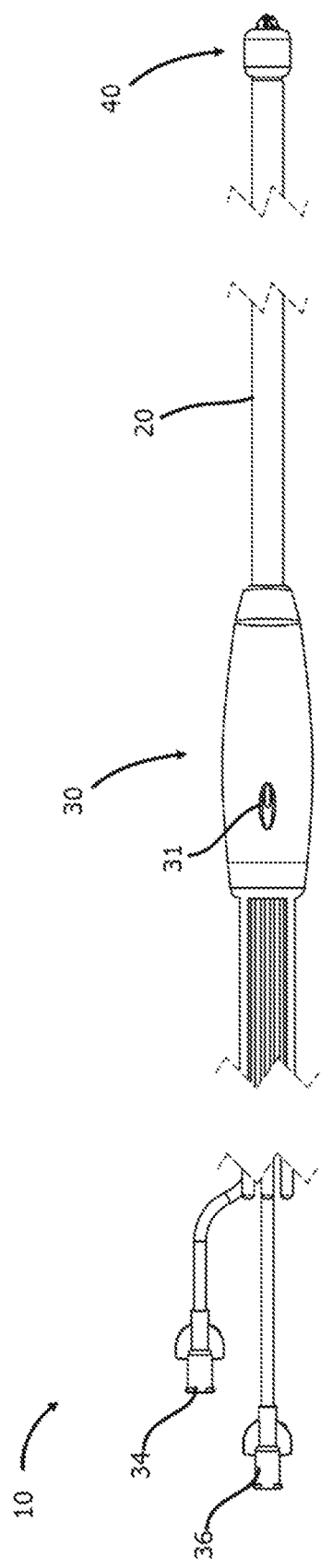
FIG. 16 is a top view of the access device of FIG. 15.

As further shown in FIGS. 1-3, the handle portion 40 optionally contains an instrument cradle 32 for affixing instrument controls to the handle portion 30. FIGS. 15-16 depict an access device 10 without an instrument cradle 32.

The access device 10 further contains a camera cable 33 extending proximally from a camera 41 in the head portion 40, through the shaft 20, and optionally into the handle portion 30. The camera cable 33 preferably extends at least 6 feet beyond the handle portion 30 and can be connected to a light and/or electrical source for operation of the camera 22. In one example, the camera cable includes optical fibers that transmit light from an external light source to the head portion 40. The camera cable 33 can also be commutatively connected to a video processing unit. In some embodiments, the access device 10 comprises controls for the camera 41 in the handle portion 30. Moreover, in some cases, the light and/or electrical source is housed within the handle portion 30.

The access device 10 can further contain one or more fluid lines, optionally extending proximally from the handle portion 40, that are fluidly connected to the one or more channels extending longitudinally through the shaft 20. For example, the access device 10 can include a balloon inflation line 34, a vacuum line 35, and/or a camera flush line 36, fluidly connected to the balloon inflation channel 24, vacuum line channel, and camera flush line 23, respectively. Each of these lines can terminate at its proximal end in a port with a suitable attachment means, such as a Luer lock connector.

Figure 4:
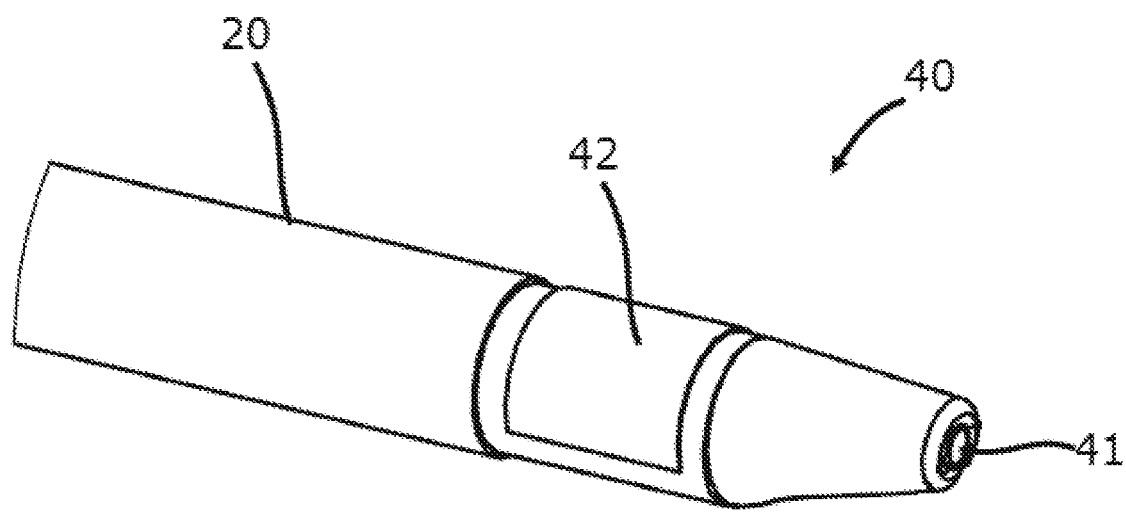
FIG. 4 is a perspective view of a distal tip portion of one embodiment of the disclosed surgical access device.
Figure 5:
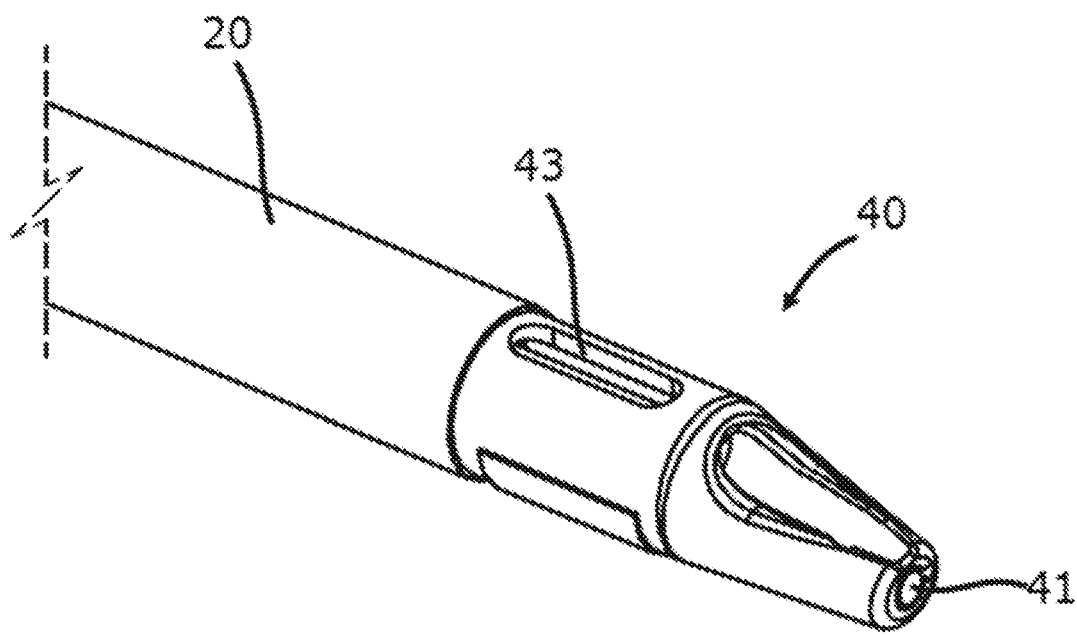
FIG. 5 is an alternate perspective view of the distal tip portion of FIG. 4.
Figure 6:
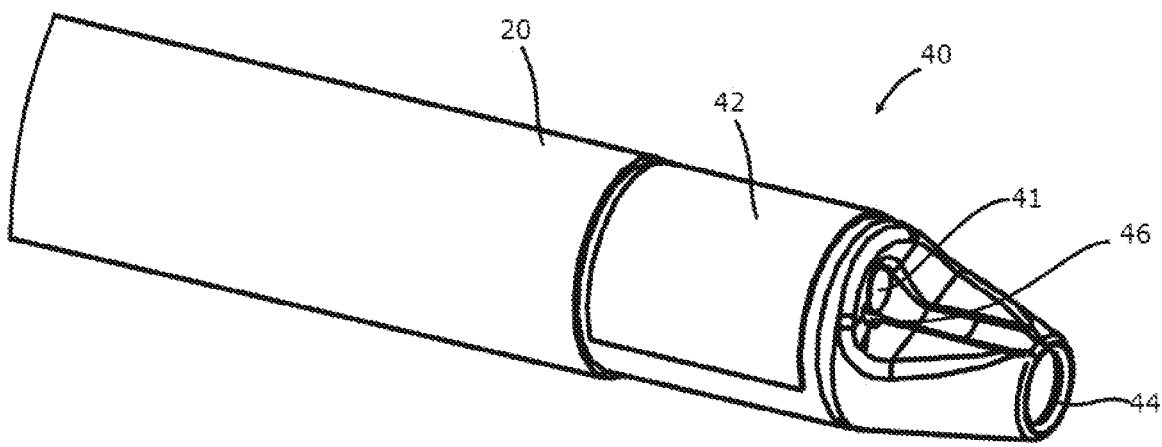
FIG. 6 is a perspective view of a distal tip portion of one embodiment of the disclosed surgical access device.
Figure 7:
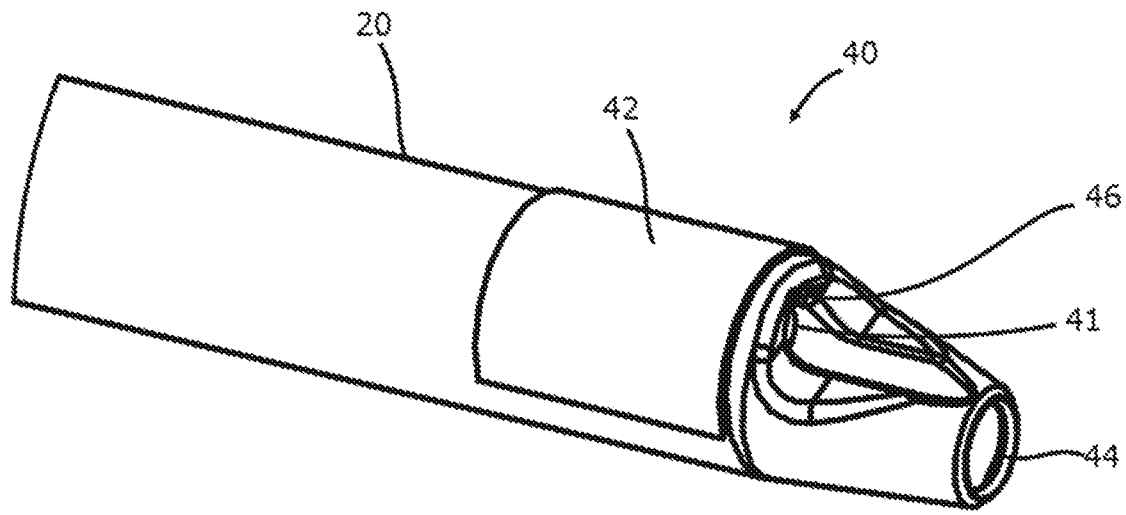
FIG. 7 is a perspective view of a distal tip portion of one embodiment of the disclosed surgical access device.
Figure 10:
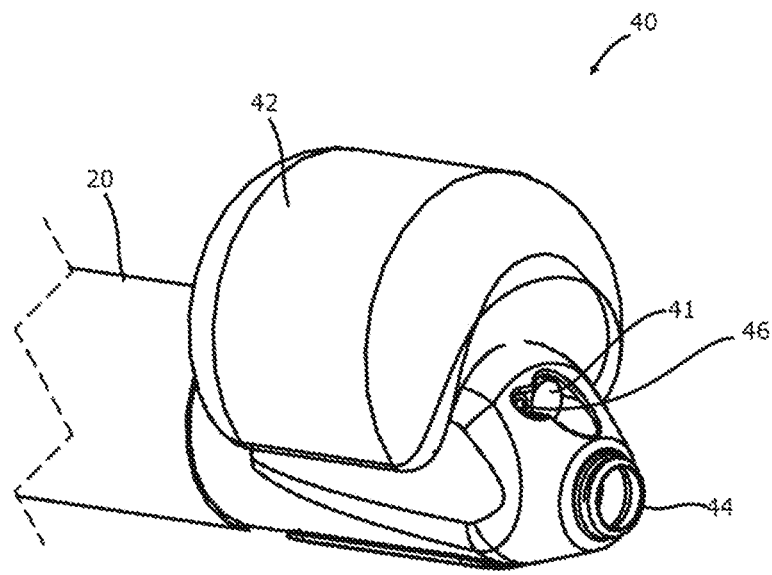
FIG. 10 is a perspective view of the distal tip portion of FIG. 8 with an inflated balloon.
Figure 11:
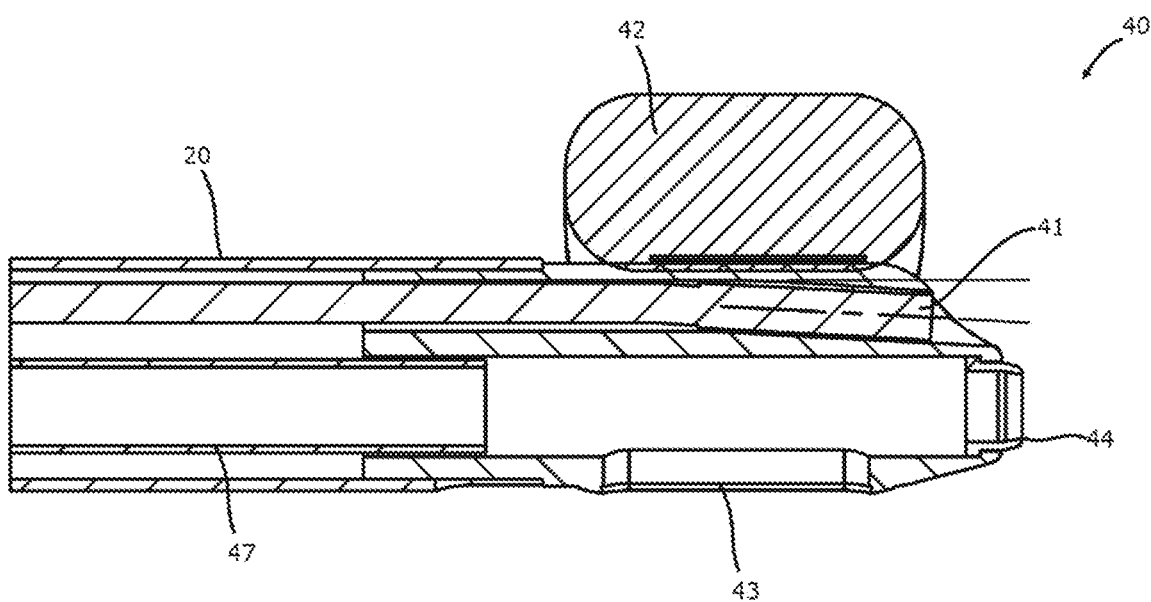
FIG. 11 is a longitudinal sectional view of the distal tip portion of FIG. 8 with an inflated balloon.
Figure 17:
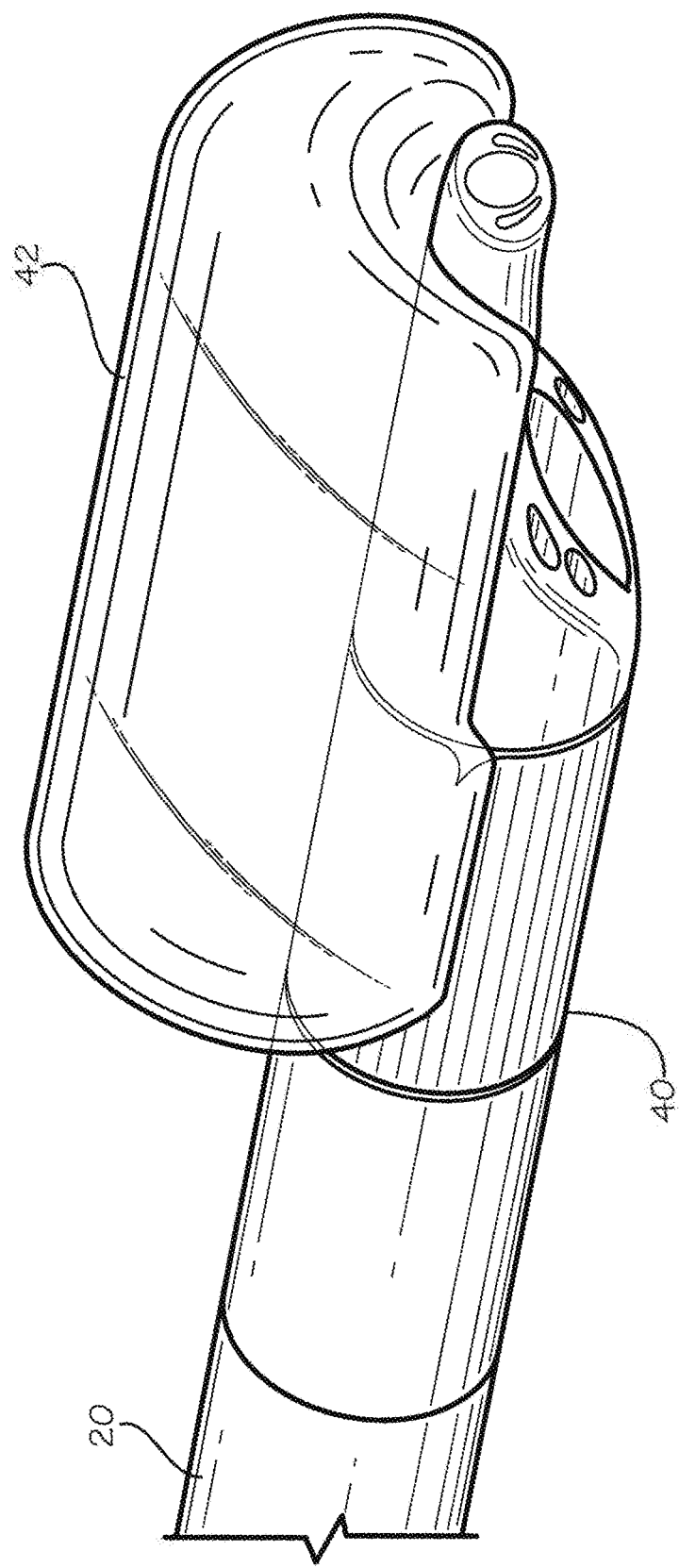
FIG. 17 is a perspective view of a distal tip portion of one embodiment of the disclosed surgical access device.

As shown in FIGS. 4-5, the head portion 40 has a top and bottom (superior and inferior) orientation. The head portion 40 can include a balloon 42 on its top surface, positioned proximally to the camera 22, fluidly connected to the balloon inflation line 34 and configured to elevate the pericardium and provide downward pressure towards the myocardium when inflated (see FIG. 10). In some cases, the balloon extends about 180 degrees along the top circumference of the head portion 40, for example as illustrated in FIGS. 10 and 17.

The balloon 42 can be inflated to assist in moving tissue from the treatment region and from view of the camera 41 to increase direct visualization and depth of view. Lifting the immediate tissue can protect the tissue from the prescribed therapy. In some cases, the balloon 42 may inflate to approximately 3 times the diameter of the shaft's 20 outside diameter. In some cases, the inflated balloon 42 provides a directed downward force to stabilize the head portion 40. The inflated balloon 42 can also assist with navigation about curvatures of tissue bodies.

During certain diagnostic and therapeutic procedures stabilization of the catheter may be required to perform the prescribed procedures. As described above, a balloon 42 can be inflated to provide downward pressure and stabilize the access device and any instruments inserted therein. The balloon 42 is configured to be inflated with a predetermined amount of fluid to expand to a particular size and shape. In one example, the balloon 42 is in fluid communication with a syringe containing the predetermined volume of fluid. The syringe is depressed to inflate the balloon and withdrawn to deflate the balloon. In another embodiment, the inflation and deflation of the balloon is controlled by a pump configured to provide or withdrawal the predetermined amount of fluid.

In some embodiments, the inflated balloon 42 provides a directed downward force to provide intimate contact between the heart tissue and an instrument (e.g., when sensing particular physical parameters such as temperature, thickness and density, ablating tissue, or injecting a substance). In some embodiments, the balloon is inflated an amount (e.g., with 3 ccm, 4 ccm, or another predetermined amount of air or saline) that provides sufficient stability of the access device 10 for treating a site without impeding navigation of the access device 10 within the pericardium. For example, the device can be advanced or retracted within the pericardial space without deflating the balloon 42. The inflated balloon 42 secures the head portion 40 in whatever location it is in when the user stops navigating the access device 10, which can simplify the procedure and significantly reduce the time required for a procedure involving multiple treatment sites. In alternative embodiments, the balloon 42 is configured to be deflated (at least partially) prior to the repositioning of the head portion 40 of the access device 20.

The configuration of the balloon 42 on the top surface of the access device 10 and/or overhanging the tip of the head portion 40 can facilitate stabilization of the access device 10. In this example, when the balloon 42 is inflated in between two abutting surfaces (such as when the device is between the epicardium and pericardium), the lower surface of the head portion 40 of the access device 10 is pressed into whatever tissue it is against. The head portion 40 of the access device is stabilized adjacent to tissue that can be treated. Stabilizing the access device 10 in a position adjacent to tissue to be treated can provide advantages over stabilization mechanisms that create space around a head 40 of an access device 10 on all sides.

Some embodiments include a balloon 42 configured to inflate about 180 degrees (e.g., 170 to 190 degrees) around the tip of the access device 10. In particular, the opening from which the balloon 42 is configured to extend is an opening that extends about 180 degrees on the top surface of the access device 10. Such a configuration has been found to reduce or minimize twisting or oscillation about the axis of the access device 10 while still allowing the lower surface of the access device 10 to contact tissue. Other opening sizes and shapes and balloon 42 configurations can cause the access device 10 to roll over on one side or the other and thus cause disorientation of the image produced by the camera 41.

Similarly, configuring the balloon 42 to extend beyond the tip of the access device 10, e.g., by a 1, 2, 3, or more millimeters, can provide stabilization. The overhang of the balloon provides additional downward pressure on the tip of the access device 10 and can also create space beyond the tip by separating two surfaces (e.g., the epicardium and pericardium) from one another beyond the tip. This separation ahead of the access device 10 can enhance visualization and improve navigation by increasing the visual depth of field.

Additionally, or alternatively, suction can be used to provide stabilization. A vacuum can be provided through an opening located proximally to the distal tip at the inferior surface. In some cases, this vacuum is applied to the instrument channel 21. In these embodiments, a molded seal located internally within the head portion 40 can be used to provide a radial seal around the instrument to mitigate any vacuum leakage. Therefore, as shown in FIG. 5, the head portion 40 can also include a vacuum port 43 on its bottom surface, e.g., arranged on the opposing side of the head portion 40 from the balloon 42, that is fluidly connected to the vacuum line 35. The vacuum port 43 can consist of one hole (e.g., slot as shown in FIG. 5) or a series of holes, configured to stabilize the head portion onto the surface of the heart when suction is applied to the vacuum line 35.

In some embodiments, the head portion 40 further includes a sensor. One example of a sensor is an ultrasound transducer (probe) used to determine the thickness and/or density of tissue. The data obtained from the ultrasound probe can be transmitted to a 3D mapping system, such as CARTO® 3 System, or ENSUE NAVX, e.g., to guide ablation and other treatments. In one example, an access device 10 includes one more metal bands configured to read a surface electrocardiogram to provide a wave form or mapping representing attributes of the tissue in the region to be treated. In one embodiment, an ablation catheter is configured with metal sensing bands for ultrasound sensing and/or a thermistor for sensing temperature. In another embodiment, a probe has piezoelectric crystals which are interconnected electronically and vibrate in response to an applied electric current. One embodiment uses a single crystal for real time depth interrogation and wall motion detection. This provides m-mode echocardiography, tracking tissue as it shrinks and expands in a single dimension. For example, viewing the data over time from left to right on a monitor, the user is able to see how the plane between the blood and the endocardium goes up and down with motion. This helps the user estimate the thickness of the wall and provides some indication of how the thickness changes with time. This provides a gross indicator of viability since there will generally not be a lot of m-mode motion of a segment of the wall over a scar but normal muscle should move in and out relatively normally. Using multiple crystals can provide additional advantages, for example, facilitating tissue characterization. Note that ultrasound capabilities can be used for ablation, injection, and other treatment application. For example, the thickness and tissue characterization information is useful in determining how long of a needle to use and how far into the heart to insert the needle during an injection. As another example, tissue characterization information is useful in ablation procedures to help users confirm that the ablation probe is targeting the right tissue.

As shown in FIGS. 4-10, the head portion 40 also includes a camera 41 at or near its distal end oriented for visualization of instruments that extend distally from the head portion 40. The camera 41 can contain both the optics and sensor necessary to capture an image. In some embodiments, only the optics of the camera 41 are located in the head portion 40. For example, light from the optics can be transmitted fiber optically to a sensor that is located proximal to the head portion 40. In some cases, the sensor is located in the handle portion 30.

In certain embodiments, the camera 41 uses a 0.9 mm to 1.6 mm diameter CMOS chip with optical fiber illumination permanently mounted in place. In certain embodiments, the camera 41 is oriented downward at an angle of 1 to 30 degrees relative to the longitudinal angle of the head portion 40 to provide an appropriate field of view. The camera 41 can use illumination fibers and/or light emitting diodes (LED's) equally spaced axially about the camera body. In one embodiment, illumination is provided through one or more fiber optic cables that provide light for the camera 41 from an external source with limited heat generated at the head 40 of the access device. For example, light generation can occur proximally (e.g., in a box on a nearby table). The use of fiber optic cables can also facilitate the provision of a greater amount of light to provide a brighter image from the camera 41 then may be possible using one or more LEDs.

As shown in FIGS. 6-10, the head portion 40 also includes a camera flush port 46, which can be used to pass saline across the camera lens in the event tissue or other matter obscures the field of view.

The head portion 40 can also contain an instrument channel opening 44 at or near its distal end that is in fluid connection with the instrument channel 21. In some embodiments, the instrument channel opening 44 is a single open lumen for which diagnostic and therapeutic instruments may pass. In some cases, this lumen has a diameter of approximately 2.0 to 4.0 mm, including about 2.5 mm to accommodate insertion of a 2.3 mm or 7 French instrument.

Figure 8:
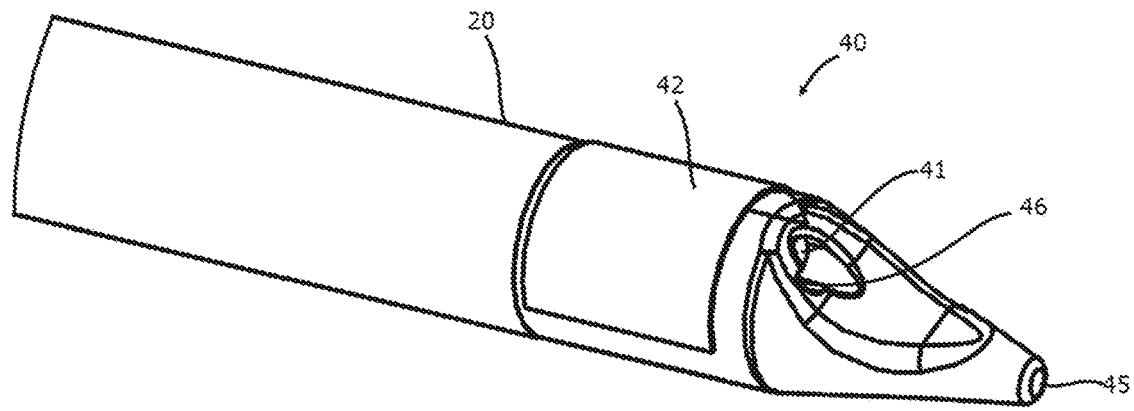
FIG. 8 is a perspective view of a distal tip portion of one embodiment of the disclosed surgical access device with a deflated balloon.
Figure 9:
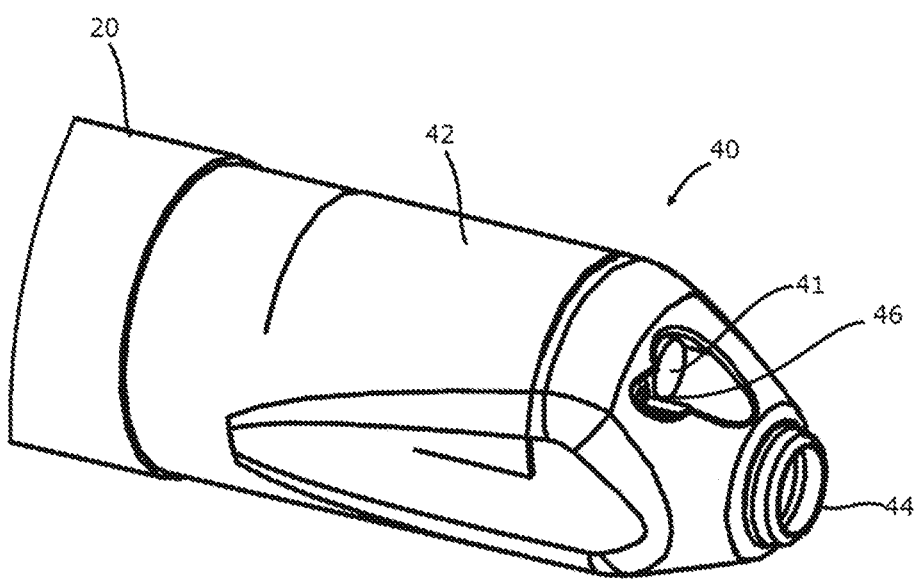
FIG. 9 is a perspective view of a distal tip portion of one embodiment of the disclosed surgical access device with a deflated balloon.
Figure 20B:
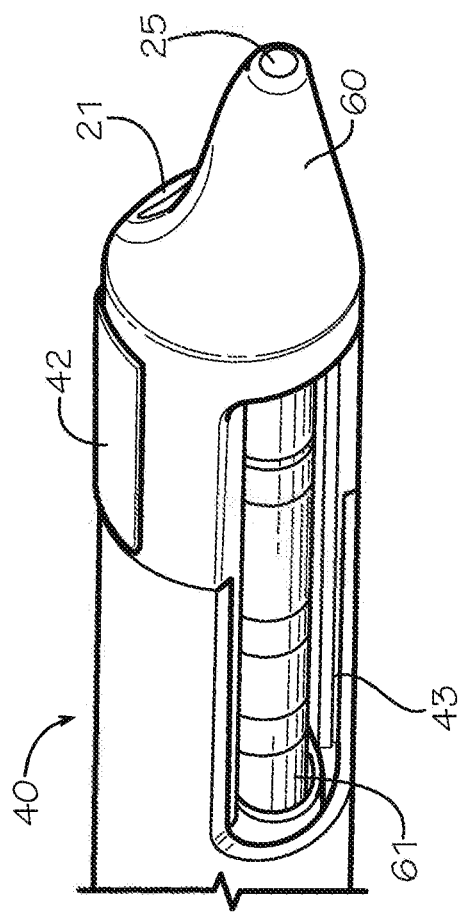
FIG. 20B is a perspective view of a distal tip portion of one embodiment of the disclosed surgical access device.

As shown in FIG. 8, the head portion 40 can alternatively contain a guide wire opening 45 at or near its distal end that is in fluid connection with a guide wire channel 25. In these embodiments, the instrument, such as an ablation catheter, does not extend distally substantially beyond the head portion 40. In some cases, the ablation catheter instead contacts the myocardium through the vacuum port 43 (FIG. 20B). The guidewire opening 45 and/or lumen can have an inner diameter suitable for use with a 0.014 inch, 0.025 inch, or 0.035 inch guidewire. One advantage to this embodiment is a low profile tip that may not need an introducer. In addition, ablation energy can be directed only towards the tissue.

As shown in FIGS. 4-10, the camera 41 is positioned above the instrument channel opening 44 or guide wire opening 45 relative to the orientation established by the balloon 42 (top) and vacuum port 43 (bottom). However, in some embodiments, the camera 41 is positioned adjacent to or below the instrument channel opening 44 or guide wire opening 45.

As can be seen when comparing FIGS. 4, 6, 21A, and 21B, the head member can be either relatively tapered or relatively blunt. Tapering can be achieved in some cases by positioning the camera 41 either distal to (FIG. 4), or proximal to (FIG. 6), the instrument channel opening 44 or guide wire opening 45. The distance between the camera 41 and the instrument channel opening 44 or guide wire opening 45 can therefore affect the amount of tapering. In some cases, the distance between the camera 41 and the instrument channel opening 44 or guide wire opening 45 is from 1 to 3 mm.

The advantage to having the camera 41 positioned distal to the instrument channel opening 44 is that it can improve visualization of the ablation since the tip of the instrument can be closer to the camera. However, it may require a separate introducer sheath since the camera 41 would be ahead of the guidewire.

In cases where the camera 41 is positioned distal to the instrument channel opening 44, the inferior surface of the tapered tip is the only surface that instruments will contact as they exit the instrument channel opening 44. In some cases, this surface slopes down with an angle of 1 to 30 degrees relative to the longitudinal angle of the head portion 40 such that the instrument is directed toward the surface of the heart with a contact point distal to the camera 41.

Figure 18:
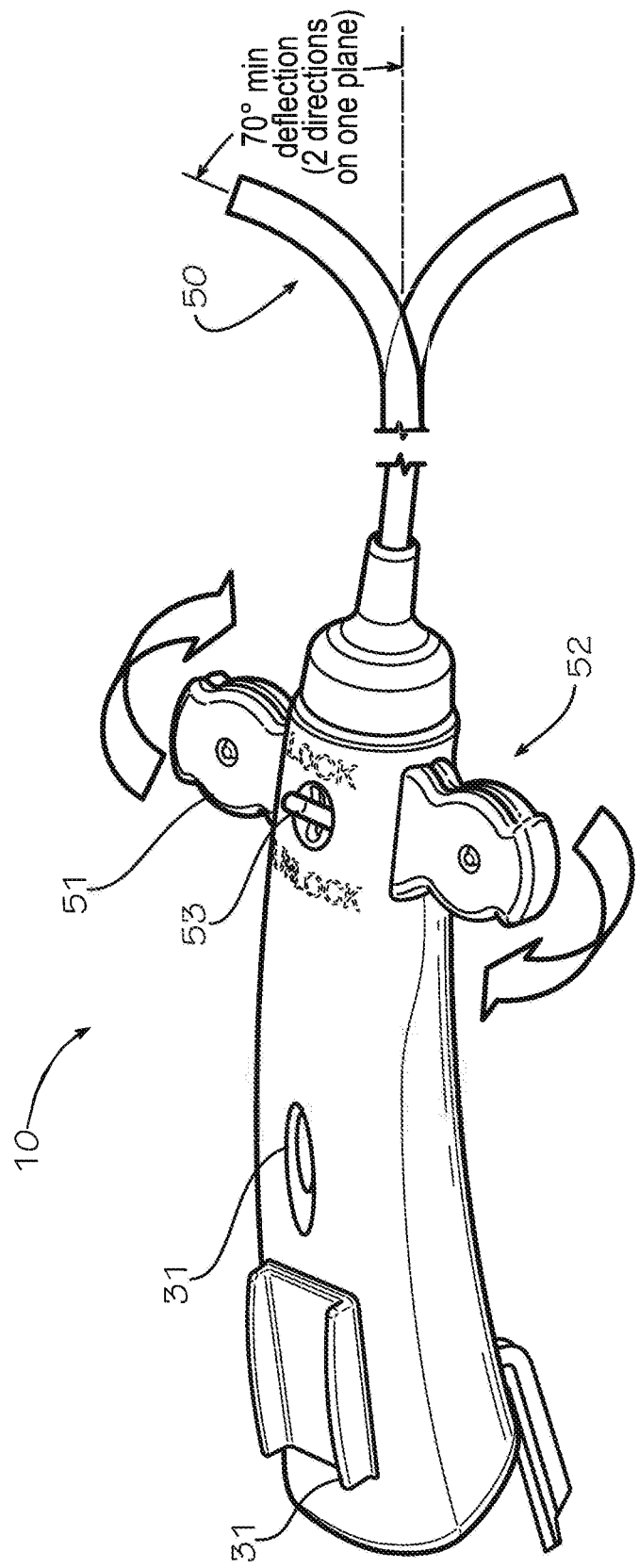
FIG. 18 is a perspective view of a distal tip portion of one embodiment of the disclosed surgical access device.

In some cases, the instruments have manual articulation and therefore can act as the articulating and guidance means. However, in other embodiments, and as shown in FIG. 18, the distal end of the shaft 20 can be articulated in at least one plane, preferably a horizontal plane. Therefore, the handle portion 30 optionally further contains controls 51, 52 for articulating the distal end of the shaft 20. Control 53 is configured to lock the articulated distal end of the shaft in particular positions, e.g., far left, far right, center, etc. The articulation occurs primarily at the tip of the catheter and may allow the tip to deflect up to 70, 80, or 90 degrees in at least one direction. In an alternative, one or more of controls 51, 52, 53 (or other appropriate controls) are used to control extension of a balloon and/or hinged shell to provide stabilization at the distal end of the shaft 20.

The articulation provided by the access device 10 can work in combination with articulation provided by the instruments. For example, the access device 10 can be maneuvered to navigate to the general area of the treatment. Next, the articulation controls on the access device 10 can be used to position the head portion 40 of the access device 10 closer to the area of the treatment. Once in the desired general area, the articulation controls on the access device 10 can be fixed. Then, the articulation controls on the instrument can be used to precisely treat a particular region within the general area of treatment. There interplay between the gross and fine articulation facilitates quick and accurate device positioning and treatment. The access device 10 can also be configured to allow instruments to extend far beyond the tip of the access device 10. This may be useful, for example, if the user needs to treat an area in the extremes of the pericardial space where access device 10 cannot itself go, e.g., wrapping around to the bottom or posterior side of heart. In such a circumstance, the user is able to push an ablation catheter or other instrument out further to get to those further positions.

The articulation of the access device 10 can be controlled using various device configurations. In one embodiment, one or more pull wires that extend down the shaft 20 of the access device 10 are used. An alternative embodiment uses a coil or braided wire configuration that is part of the assembly of the shaft 20.

FIG. 18 depicts a distal tip portion of one embodiment of the access device 10. In this embodiment, the access device 10 includes lever arms 51 and 52 that connect to opposing sides of the distal tip 50 of the access device. The lever arms 51, 52 attach to the respective opposite sides of the distal top 50 via pull wires (not shown) and are used to deflect the distal tip 50 in left direction or a right direction in a single plane. One or more such lever arm/pull wire configurations can be used to implement one or more articulation directions of the distal tip 50. FIG. 18 illustrates deflections of the distal tip 50 of 70° min in two directions in a single plane.

Figure 19B:
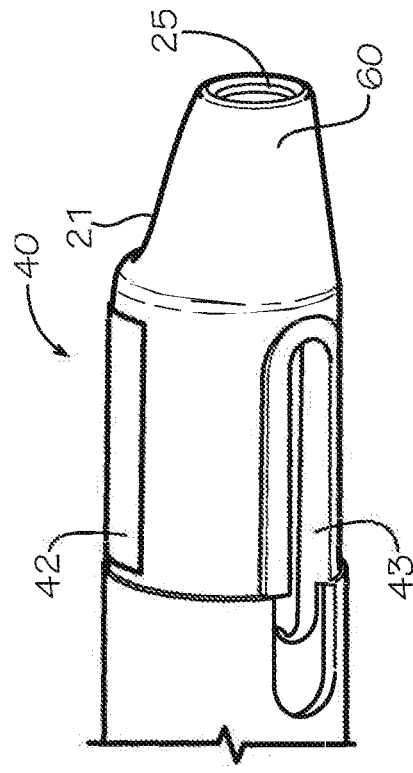
FIG. 19B is a perspective view of a distal tip portion of one embodiment of the disclosed surgical access device.
Figure 19A:
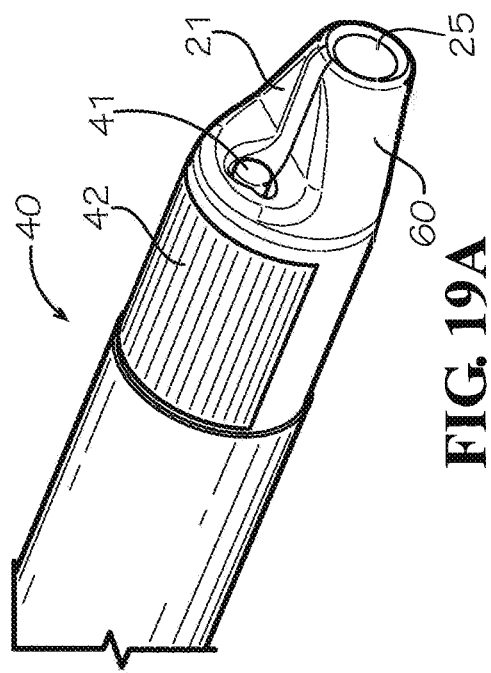
FIG. 19A is a perspective view of a distal tip portion of one embodiment of the disclosed surgical access device.

FIGS. 19A and 19B depict a distal tip portion 60 of a head 40 of one embodiment of the access device 10. The distal tip portion 60 is tapered and has an instrument opening 21 for an instrument to perform a treatment. The camera 41 is positioned within the head 40 and provides a forward-facing view of the instrument opening 21.

Figure 20A:
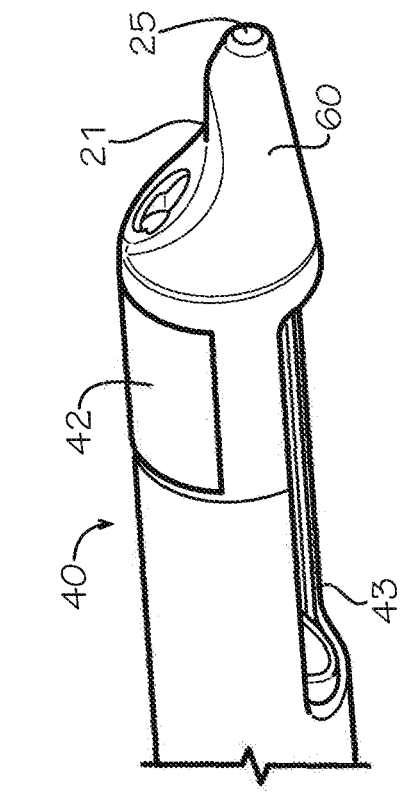
FIG. 20A is a perspective view of a distal tip portion of one embodiment of the disclosed surgical access device.

Similarly, FIGS. 20A and 20B depict the distal tip portion 60 of the head 40 in another embodiment of the access device 10. In this embodiment, the vacuum port 43 opens to the instrument channel 21 on the interior of the access device 10, allowing a treatment instrument 61, such as an ablation catheter, to treat tissue through the vacuum port 43.

Figure 21A:
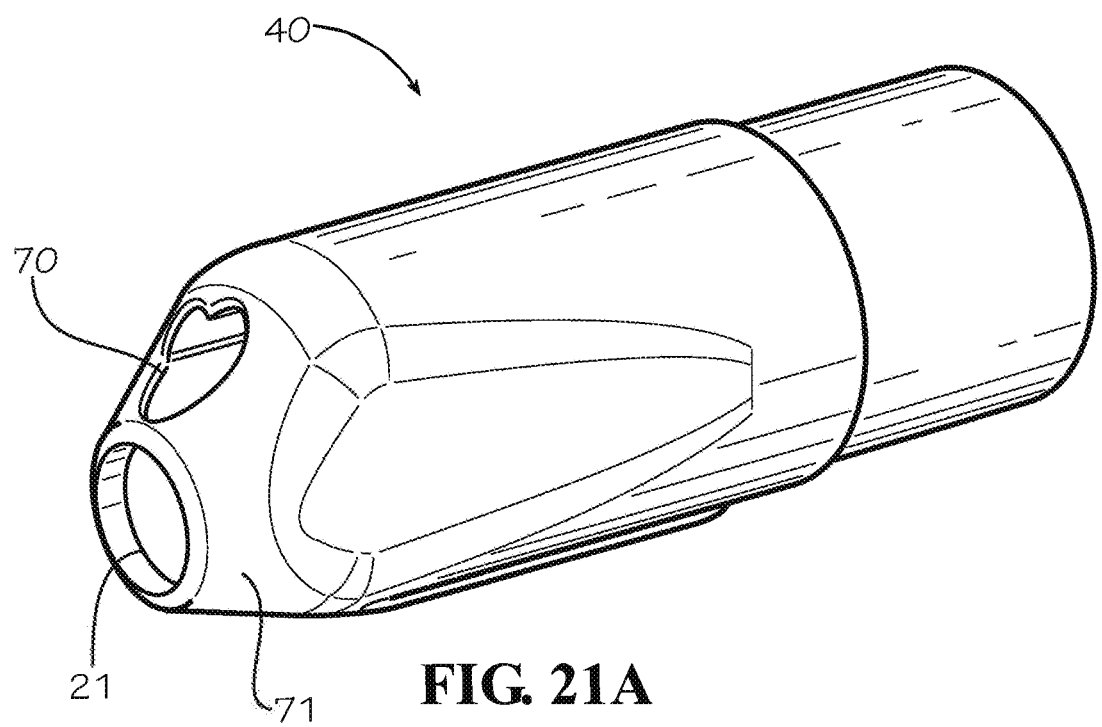
FIG. 21A is a perspective view of a distal tip portion of one embodiment of the disclosed surgical access device.
Figure 21B:
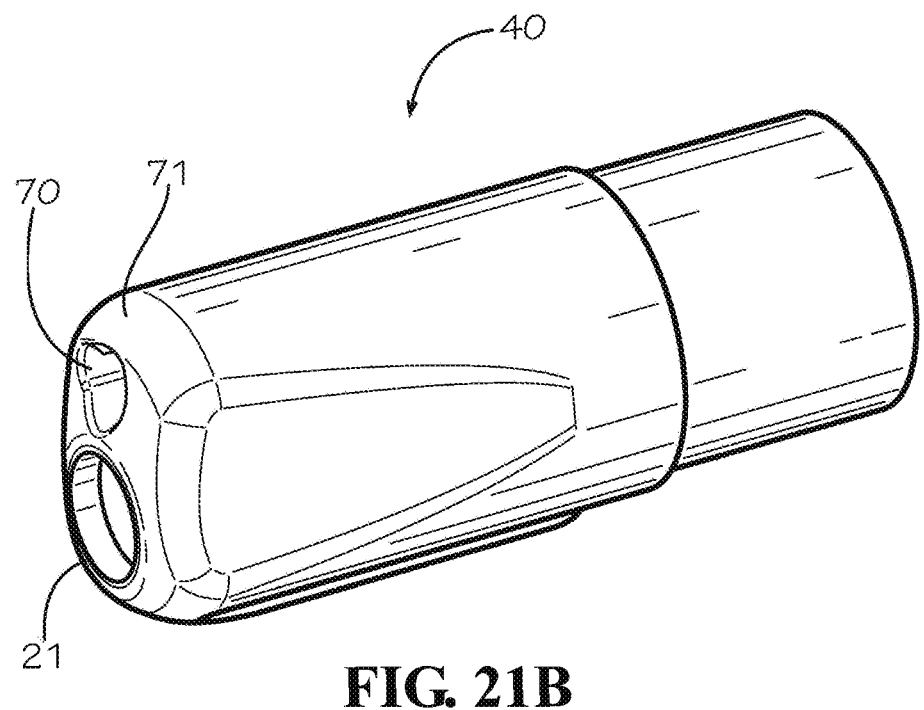
FIG. 21B is a perspective view of a distal tip portion of one embodiment of the disclosed surgical access device.
Figure 22:
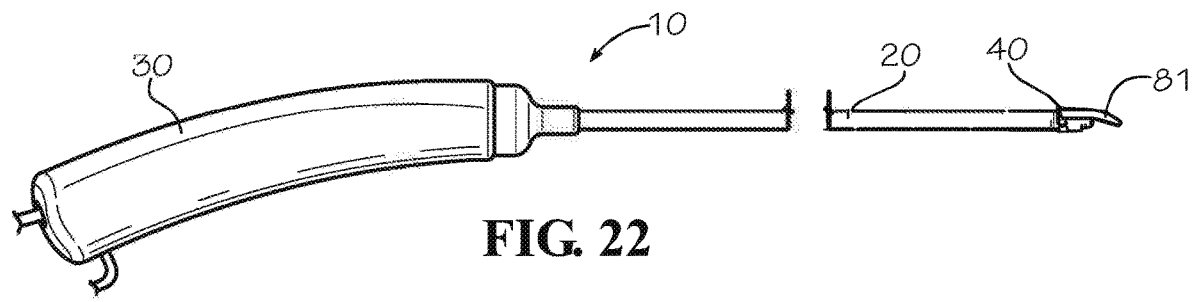
FIG. 22 is a perspective view of the access device according to another embodiment.

FIGS. 21A and 21B depict the distal tip portion 60 of the head 40 of additional embodiment of the access device 10. In FIG. 21A, the distal tip portion 60 has a tapered portion that defines additional opening 70 to provide camera visibility and/or provision of a fluid. In FIG. 21B, the distal tip portion 60 has a relatively blunt portion 71 and the additional opening 70 is on a front surface of the distal tip 60 adjacent the instrument channel 21 rather than being on the relatively blunt portion 71.

FIGS. 22-25 illustrate the access device 10 according to another embodiment in which the head 40 includes a hinged shell 81. The hinged shell attaches to the head 40 at hinges 82, which enable the hinged shell 81 to extend away from the head 40. In the example of FIGS. 22-25, the hinge shell 81 is attached to the top surface of the head 40 and configured to extend upward adjacent to the top surface of the head 40 without extending adjacent to the bottom surface of the head 40. The hinged shell 81 also includes a guidewire opening 84 through which guidewire 90 (FIG. 24) extends during the initial insertion of the access device 10. In other words, the guidewire 90 is first inserted into the treatment area and then the access device 10 is inserted around the guidewire 90 with the guidewire 90 extending through a guidewire channel in the access device 10 and through the guidewire opening 84. In this way, the guidewire opening 84 secures the hinged shell 81 in place during insertion and/or forward movement of the access device 10. Alternative embodiments do not include or use a guidewire opening 84 in the hinged shell 81.

In embodiments of the invention, the upper surface of the hinged shell 81 has a smooth, hard surface. In embodiments of the invention, the upper surface is curved to reduce friction during insertion, movement, and articulation of the access device head 40. In one embodiment, the hinged shell 81 is a canopy that at least partially surrounds the head 40 of the access device 10 when the hinged shell 81 is in a closed position. The hinged shell 81 can have a fingernail shape. The hinged shell 81 can have a shape that gradually narrows towards the tip 87. The tip 87 of the hinged shell 81 can extend distally beyond the distal end 88 of the head 40. The distal extension of the tip 87 beyond the distal end 88 can improve the amount of space created when the hinged shell 81 is extended upward away from the head 40. For example, it can provide space for an ablation catheter 100 to ablate tissue and/or provide space for an injection needle to inject a substance. The tip 87 of the hinged shell 81 can be anti-reflective, opaque, or flat black to improve lighting and visualization conditions during use of the access device.

In the example of FIGS. 22-26, the hinged shell 81 further includes a camera 83 on the access device 10. The camera 83 is attached on an underside of the hinged shell 81 (for example under the tip 87 of the hinged shell) and oriented generally in a downward orientation to capture images of the treatment region and/or instruments used to perform treatment. The orientation of the camera can be selected based on an appropriate angle when the hinged shell 81 is in an extended position/a closed position, or both. For example, the camera 83 can be mounted in the hinged shell 81 at a 40 degree. In one example, the downward or closed position of the hinged shell 81 places the camera at a 70 degree angle relative to the hinged shell 81 hinge point. With the hinged shell 81 in the up or open position, the camera is projected out at 30 degree angle relative to the hinged shell 81 hinge point. This provides an optimal field of view when the hinged shell 81 is in an extended position. In one embodiment, fiber optic cable provides lighting that extends axially from the access device 10 while the camera provides an angled view from the hinged shell 81 of the region of the human body. This exemplary camera orientation can facilitate improved spatial reconciliation, allowing the user to see the treatment instrument and a topographical view of where the treatment instrument can be used to provide treatment with a region, for example, in relation to anatomical structures that should be treated or avoided.

The camera 83 can involve a CMOS chip with optical fiber illumination permanently mounted in place. For example, illumination fibers can be equally spaced axially about the camera body. In one embodiment, illumination is provided through one or more fiber optic cables that provide light for the camera 83 from an external source without generating heat at the head 40 of the access device 10. For example, light generation can occur proximally (e.g., in a box on a nearby table).

Figure 23:
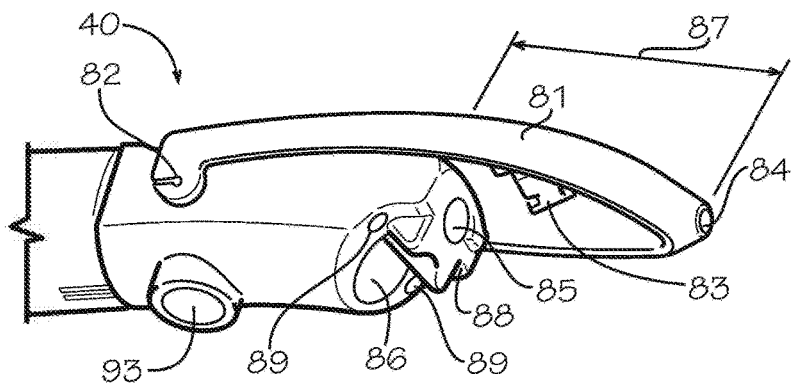
FIG. 23 is a perspective view of a distal tip portion of the embodiment of FIG. 22.
Figure 24:
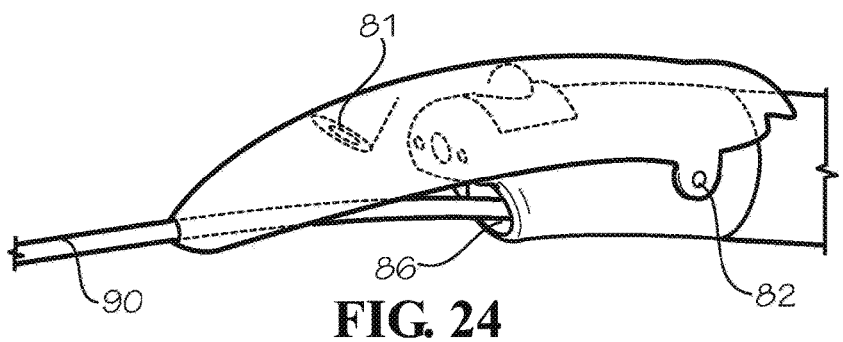
FIG. 24 is a perspective view of a distal tip portion of the embodiment of FIG. 22 with a guide wire inserted.

The head 40 also includes openings 85, 86, 89 configured at the end of channels that provide passages for treatment instruments, diagnostic probes, light-providing fiber-optic cables, other instruments, pull wires and other articulation mechanisms for articulating the head and/or moving the hinged shell 81, and/or fluids for inflating a balloon. In one example, instrument opening 86 is configured to allow an ablation catheter 100 (FIG. 25) to extend to treat tissue in a treatment region of the patient and openings 89 are configured to provide a light from light channels (e.g., with fiber optic cables). FIG. 23 shows an ultrasound transducer 93 mounted on the head 40. The ultrasound transducer 93 is commutatively coupled, e.g., via a wire running through shaft 20 (e.g., through a channel through the shaft 20), to ultrasound processing equipment and/or displays. The position of the ultrasound transducer 93 on the head 40 can vary depending upon the intended use of the access device 10. As examples, the ultrasound transducer 93 can be positioned adjacent to one or more of the openings 85, 86, 89. If positioned adjacent an instrument opening 86, the ultrasound transducer can specifically target the tissue about to be treated, being treated, or having been treated by a treatment instrument that extends from the instrument opening 86.

Figure 25:
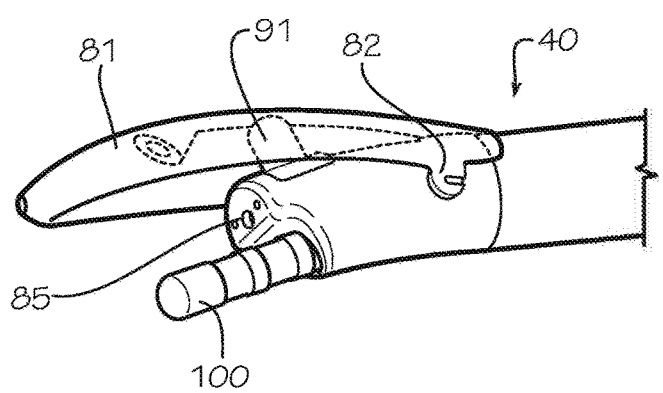
FIG. 25 is a perspective view of a distal tip portion of the embodiment of FIG. 22 with an ablation catheter inserted.
Figure 26:
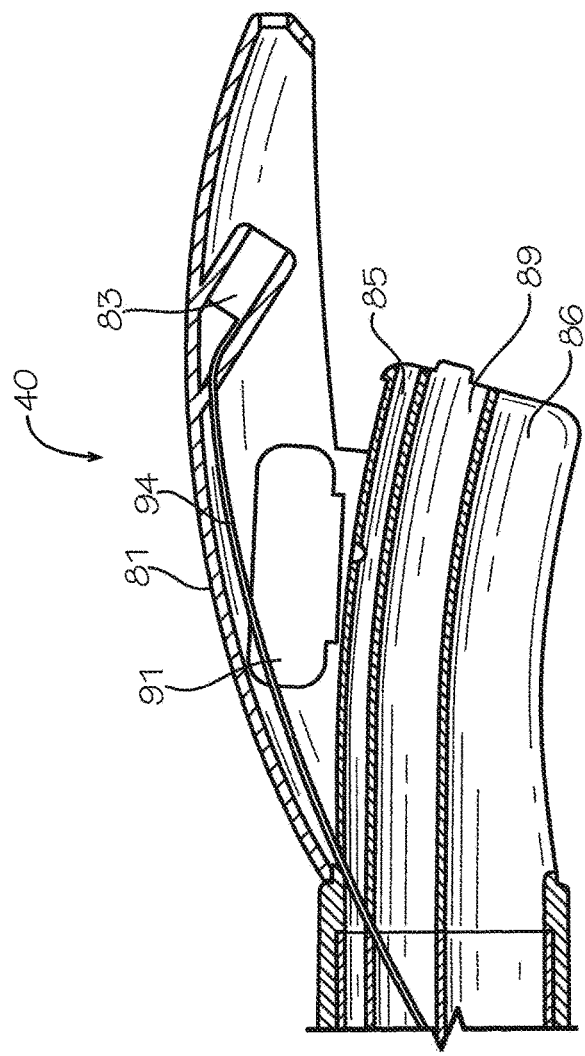
FIG. 26 is a longitudinal sectional view of the distal tip portion of FIG. 22 with the hinged shell raised.

FIG. 25 illustrates the hinged shell 81 in an extended or raised position, i.e., where the distal end of the hinged shell 81 has been extended from the access device head 40. Various features can be used to raise and lower the hinged shell 81. In one example, one or more pull wires connect the hinged shell 81 to hinged shell controls. The hinged shell controls are configured to pull, hold, release, and extend the pull wire to extend and close the distal end of the hinged shell 81 away from the head 40. A hinged plate affixed to the top of the distal end of the head 40 can be actuated by a pull wire. In an alternative embodiment, the hinged shell 81 is raised or lowered by a balloon 91 being inflated and deflated, respectively beneath the hinged shell 81. The inflation/deflation of the balloon 91 can be controlled, for example, using a syringe. The hinged shell controls can be located on the handle 30. In one embodiment, a hinged shell control is a thumb toggle on the handle 30.

The hinged shell 81 is generally configured to provide one or more functions provided by the balloon 42 described with reference to other embodiments of the access device 10, as well as additional functions. Attributes of exemplary hinged shells can provide various advantages over certain balloon-based access devices 10. For example, the relative hardness of the hinged shell 81 can provide greater stability than a relatively softer balloon. As another example, the hinged shell 81 can be controlled using pull-wire controls or other controls based on mechanical movements rather than injection and withdrawal of a fluid. Such mechanical-based controls may be easier, faster, and/or more convenient for some users. In addition, the fabrication and assembly of a device that uses a hinged shell 81 may be easier to fabricate, assemble, and/or prepare for use than an access device 10 that includes a balloon.

Figure 27:
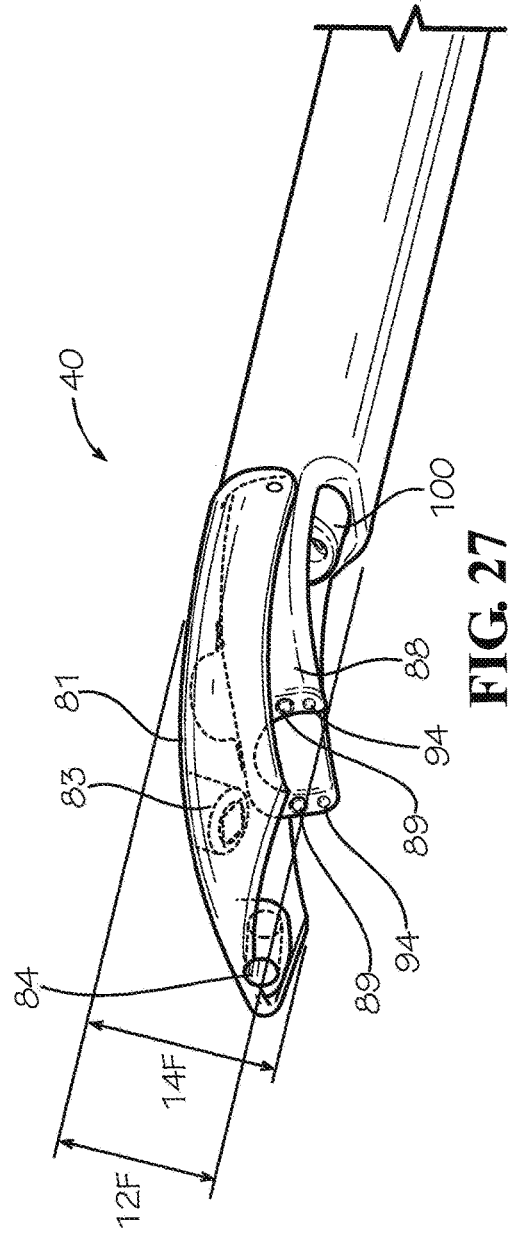
FIG. 27 is a perspective view of an alternative embodiment of the access device configured to have a low profile.

FIG. 27 is a perspective view of an alternative embodiment of the access device configured to have a low profile. In this example the diameter of the access device can be 14 French or smaller. The relatively smaller diameter is achieved in this example using various design elements. For example, positioning and sizing the openings 89, 94 to the sides of the instrument opening 86 and having the corresponding channels in the similarly positioned can facilitate a slimmer profile. In one example, openings 89 are configured to provide a light from light channels (e.g., with fiber optic cables) and openings 94 are configured at the end of lumens through which pull wires or other articulation mechanisms run to enable control of articulation of the head 40 (e.g., allowing left or right articulation movement). In addition, the tip portion 88 of the head 40 is angled down from the longitudinal access. The opening along the bottom of the tip portion 88 reduces the size of the device (e.g., limiting the distance from the top of the shaft to the bottom of the tip portion 88 to 16 French or smaller). Accordingly, this embodiment accommodates a distal tip 88 configured to angle an instrument downward towards the tissue to be treated while minimizing the profile of the access device.

The access device 40 can include a channel and corresponding opening to provide saline or another fluid to flush away tissue that is blocking or impairing the view in front of camera 83. In some embodiments of the invention, such as a flush channel is provided through both the shaft 20 and through the hinged shell 81. For example, a flush channel can be provided via a tube that extends through a channel in the shaft of the access device 10 and into a continuation of the channel that runs through the hinged shell 81 to an opening proximate the camera 83. In another example, a fluid channel in the shaft 20 and a fluid channel in the fluid connection mechanism, such as flexible connector, that maintains the connection between the fluid channels when the hinged shell 41 is raised and/or lowered. In one example, the flush channel extends distally beyond the camera 83 within the hinged shell 81 and is configured to direct fluid back proximally at the lens of the camera 83. Such a configuration may involve a curve or bend in the channel to direct the fluid in an appropriate direction.

Figure 28:
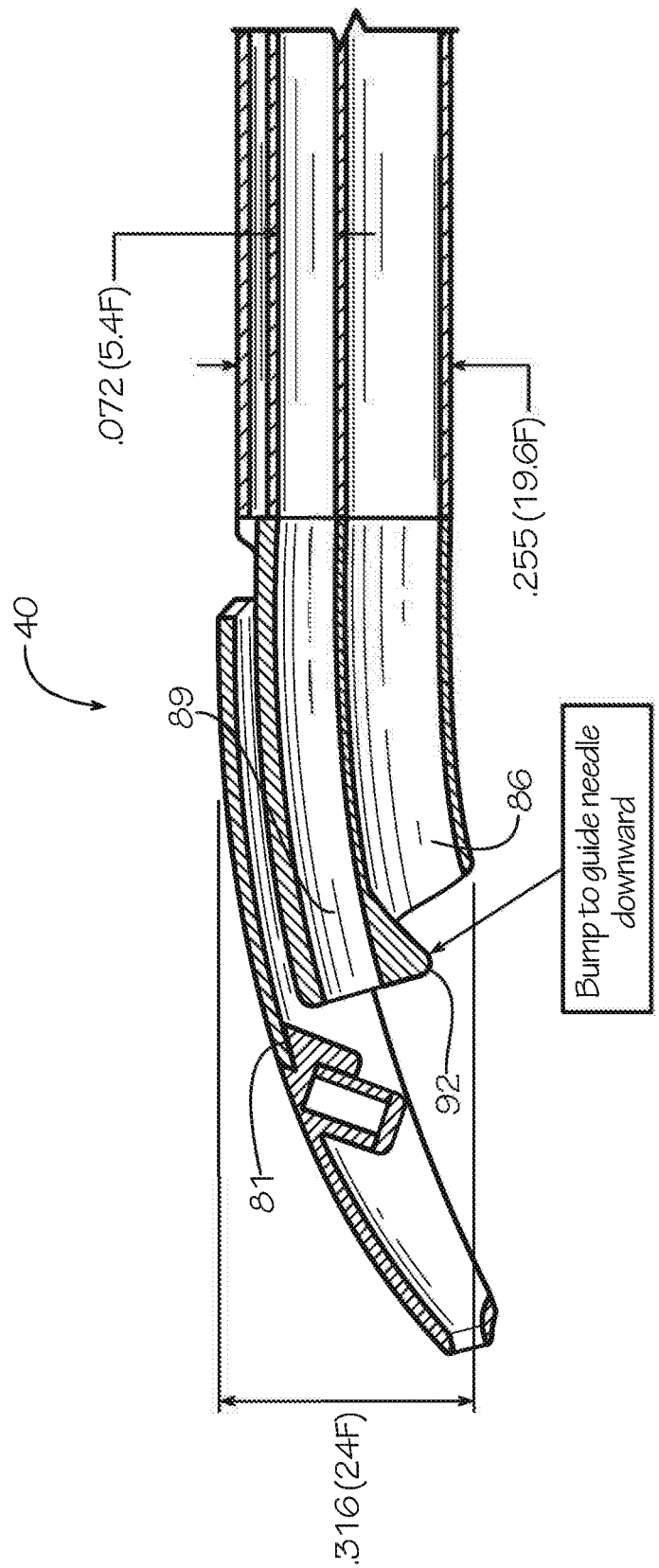
FIG. 28 is a longitudinal sectional view of the distal tip portion of an access device having a projecting bump to guide an instrument at a downward angle towards tissue.

FIG. 28 is a longitudinal sectional view of the distal tip portion of an access device having a projecting bump 92 to guide an instrument at a downward angle towards tissue. Such a bump or other projection 92 can, for example, be used to guide an injection instrument such as a needle at an angle (e.g., at a 30, 35, 40, 45, or 50 degree angle from the axis of the instrument channel in the shaft of the access device). The angle can be created by a combination of an angle in the tip of the shaft and a projection at the opening. The angle can be selected for the particular application of the access device. For example, a 45 degree angle may be selected as appropriate for certain injection applications.

The access devices 10 described herein can be manufactured using various manufacturing techniques. The shaft 20 can comprise polymer and metal materials of various diameters to ensure flexibility and guidance. It can be fabricated using common multi-layer catheter manufacturing techniques where stainless steel wire braids of particular, unique designs that afford specific hoop strength and flexibility when applied to specific polymer extrusions of particular and uniquely specified diameters, wall thicknesses and durometer to form a unique catheter assembly.

The shaft 20 is preferably designed to articulate approximately 0 to 160 degrees inclusive in a lateral plane, including 45 to 120 degrees, and 0 to 100 degrees. The shaft 20 can have a length of 1 to 5 feet, including 30 cm to 60 cm.

The head portion 40 can be fabricated using biocompatible polymer materials employing common injection mold processes and/or by additive manufacturing processes similar to stereolythogrophy.

The handle portion 30 can be produced using various molded components of common biocompatible materials.

A particular catheter design will have components for providing particular information to the user about the tissue being treated before, during, and after a therapeutic or diagnostic procedure is performed. This can involve a transducer that transmits and receives ultrasonic wave forms. An algorithm would be employed to determine the waveforms transmitted and received to develop the correct information to the user.

Preferably, the access device 10 is comprised of materials that are able to withstand the temperature, moisture and pressure of typical sterilization processes such as ethylene oxide and Gamma radiation needed for fields like the thoracic cavity. Also, the shaft 20 and head portion 40 are preferably comprised of biocompatible materials that do not create extensive friction with the surrounding tissues.

The access device 10 described herein enables a variety of new methods of providing treatment to patients. Exemplary methods of treatment include those that provide treatment within the pericardium under direct visualization. One such method involves inserting a guidewire 90 through a 2 centimeter (cm) or smaller sub-xiphoid incision in the skin of the human body or via percutaneous needle and guide wire access and into the pericardial space. The method next involves inserting a head 40 of the access device 10 into the pericardial space using the guidewire 90, wherein the access device 10 comprises a shaft 20 comprising a proximal end and a distal end, the shaft 20 defining a lumen comprising channels extending longitudinally between the proximal end outside of the human body and the distal end attached to the head 40 in the pericardial space. The method further involves determining a region of the heart to treat based on a mapping of the heart. For example, this can involve determining which region to treat using an ultrasound transducer positioned at the head 40 and configured to determine tissue thickness and/or density.

The method further involves positioning the head 40 of the access device 10 adjacent the portion of the heart to treat. For example, the user can push and pull the access device 10 using the handle 20 to push the head 40 of the access device 10 further into the pericardial space or pull the head 40 of the access device 10 back within the pericardial space. The user can additionally or alternatively articulate the access device to move the head 40 of the access device 10 left or right within the pericardium. In some embodiments, a camera 41, 83 of the access device 10 is activated to provide images to aid in the insertion and/or positioning of the access device 10.

The method then involves extending a portion (e.g., a balloon 42 or hinged shell 81) of the access device 10 away from a top surface of the access device 10 to separate the portion of the heart to treat from a surrounding portion of the pericardium.

The method further involves viewing an image of the portion of the heart to treat adjacent the head of the access device. The image of the portion of the heart to treat captured by a camera 41, 83 at the head 40 of the access device 10. For example, the camera can capture video images of the portion of the heart and/or images of an instrument inserted through the access device 10 to treat the portion of the heart. The images are used to confirm that the tissue that will be treated is the intended tissue and/or that arteries or other anatomical structures will not be inadvertently treated.

The method further involves treating heart tissue in the portion of the heart to treat. In one example, treating the heart tissue involves using an electrophysiology (EP) ablation catheter inserted through one of the channels in the shaft 20 of the access device 10 to ablate the heart tissue. In another example, treating the heart tissue involves injecting a substance adjacent to or in the portion of the heart using an injection catheter inserted through one of the channels in the shaft 20 of the access device 10. As a specific example, this can involve positioning the access device 10 at particular angle (e.g., approximately 45 degrees) relative to the surface of the tissue and injecting a substance adjacent to or in the portion of the heart using an injection catheter. The distal end of the instrument channel 21 can include an angle that causes an instrument passed through the instrument channel 21 to project at a downward angle relative to the axis of the shaft to better engage tissue. Treating the heart tissue can additionally or alternatively involve articulating a treatment catheter to precisely position a tip of the treatment catheter relative to the heart tissue.

The method can involve treating one or more specific areas of the heart. To do so, the device is moved to a desired area, gross articulations are made using articulation controls on the access device, and fine articulations are made using articulation controls on a treatment instrument such as an ablation catheter or injection probe. After treating one area of the heart, the access device 10 is moved to treat one more additional areas of the heart. For each area, the user repositions the access device 10 and then performs gross and fine articulations as described above. Moreover, the balloon 42, hinged shell 81, or other component that is used to create space and/or stability can be retracted/closed to facilitate the movement from one area to the next. For example, a movement of the access device 10 can involve retracting the balloon 42 or hinged shell 81 to the top surface of the access device 10, moving the access device 10 within the pericardial space, re-extending the balloon 42 or hinged shell 81 away from the top surface of the access device 10, and/or performing the gross and fine articulations described above.

The exemplary methods described above enable users to provide medical treatment with better success, efficiency, and ease than prior techniques. A user is able to view information on a screen during the procedure that allows the user to confirm that the treatment will only affect the desired portions of the anatomy. For example, such a screen may show the user a view from the camera, a mapping system such as the CARTO®3 System, or ENSITE NAVX or from an ultrasound transducer, information from sensors on an ablation or other treatment catheter, the patient's EKG, and other appropriate information. The user is then able to precisely position the access device 10 and treatment instrument to treat one or more specific areas. In many instances, the user will also be able to confirm that the treatment (e.g., ablation, injection, etc.) has been successful based on the visualization and other information provided on the screen.

A number of aspects of the systems, devices and methods have been described. Nevertheless, it will be understood that various modifications may be made without departing from the spirit and scope of the disclosure. Accordingly, other aspects are within the scope of the following claims.

What is claimed is:

1. An access device configured for guiding instruments to a region within a human body, the access device comprising:
   a shaft comprising a proximal end and a distal end, the shaft defining a lumen comprising channels extending longitudinally between the proximal end and the distal end, the channels comprising an instrument channel and a guide wire channel;
   a head attached to the distal end of the shaft, the head comprising a top surface, a bottom surface opposite the top surface, and a port configured to allow an instrument extended through the instrument channel to interact with the region of the human body;
   a hinged shell attached to the top surface of the head and configured to pivot toward and away from the top surface of the head;
   a guidewire opening in the hinged shell sized to receive a guide wire extending from the guide wire channel, the guide wire thereby holding the hinged shell in a closed position when the guidewire extends through the guidewire opening; and
   a camera mounted on an underside of the hinged shell between a distal end of the hinged shell and the port and commutatively coupled to a camera cable extending through the shaft, the camera oriented to capture images of the region of the human body.

2. The access device of claim 1 wherein the port is on the bottom surface of the head and the instrument channel connects to a vacuum.

3. The access device of claim 1, wherein the channels further comprise a vacuum channel separate from the instrument channel, wherein the vacuum channel connects to a vacuum, wherein the head defines a vacuum port on the bottom surface of the head, the vacuum port fluidly connected to the vacuum channel.

4. The access device of claim 1, wherein the instrument channel is configured to receive one of a diagnostic probe, an ablation instrument, and an injection instrument configured to deliver an injectable.

5. The access device of claim 1, wherein the channels further comprise a diagnostic probe channel configured to receive an ultrasound transducer probe for measurement of tissue thickness and density in the region of the human body.

6. The access device of claim 1, wherein the head further comprises an ultrasound transducer probe configured to determine tissue thickness and density in the region of the human body, wherein the ultrasound transducer probe is commutatively coupled to a diagnostic cable extending through the shaft.

7. The access device of claim 6, wherein the ultrasound transducer probe comprises electronically interconnected piezoelectric crystals that vibrate in response to an applied electric current.

8. The access device of claim 1, wherein the camera comprises a complementary metal-oxide semiconductor (CMOS) chip with optical fiber illumination.

9. The access device of claim 8, wherein the access device comprises fiber optic cable configured to provide illumination for the camera.

10. The access device of claim 1, wherein the camera is oriented at an angle of 1 to 30 degrees relative to a longitudinal axis of the head.

11. The access device of claim 1, wherein the channels further comprise a camera flush channel and the head further comprises a camera flush port configured to pass fluid across a camera lens of the camera.

12. The access device of claim 1, wherein the shaft and head of the access device are sized for insertion through a 2 centimeter (cm) or smaller opening in skin of the human body and pericardium during a surgical procedure, cardiology procedure, or EP cardiology catheterization laboratory procedure on the heart.

13. The access device of claim 1, further comprising a handle comprising controls configured to enable manual control of articulation of the head of the access device in at least one plane, the articulation comprising the head deflecting in at least one direction.

14. The access device of claim 1, further comprising a pull wire extending from the hinged shell to a hinged shell control, wherein the hinged shell control is configured to pull the pull wire to extend a distal end of the hinged shell away from the head.

15. The access device of claim 14, wherein the hinged shell control is a thumb toggle on a handle of the access device.

16. The access device of claim 1, wherein the hinged shell has a fingernail shape.

17. The access device of claim 1, wherein a tip of the hinged shell extends distally beyond the distal end of the head.

18. The access device of claim 1, wherein the access device comprises fiber optic cable configured to provide illumination for the camera.

19. The access device of claim 18, wherein the fiber optic cable provides lighting that extends axially from the access device, while the camera provides, from the hinged shell, an angled view of the region of the human body.

20. The access device of claim 1, further comprising a balloon attached to the head and in fluid communication with a balloon inflation channel extending through the lumen.

21. The access device of claim 1, wherein the channels further comprise a camera flush channel and the head further comprises a camera flush port configured to pass fluid across a camera lens of the camera.

22. The access device of claim 1, the hinged shell does not movable move beyond the bottom surface of the head.

23. The access device of claim 1, wherein the camera is oriented generally in a downward direction with respect to the underside of the hinged shell.

24. The access device of claim 1, further comprising an ultrasound probe positioned at the head.

25. The access device of claim 24, wherein the ultrasound probe comprises a probe inserted through a diagnostic probe channel through the shaft.

26. The access device of claim 24, wherein the ultrasound probe is attached to the head.

27. The access device of claim 26, wherein the ultrasound probe is mounted on the head.

* * * * *